(12) United States Patent
Xie et al.

(10) Patent No.: US 8,101,592 B2
(45) Date of Patent: Jan. 24, 2012

(54) HEXAHYDRO-CYCLOOCTYL PYRAZOLE CANNABINOID MODULATORS

(75) Inventors: Mingde Xie, Belle Mead, NJ (US); Fina Liotta, Westfield, NJ (US); Huajun Lu, Bridgewater, NJ (US); Meng Pan, Neshanic Station, NJ (US); Michael P. Wachter, Bloomsbury, NJ (US)

(73) Assignee: Janssen Pharmaceutica N.V., Beerse (BG)

( * ) Notice: Subject to any disclaimer, the term of this patent is extended or adjusted under 35 U.S.C. 154(b) by 0 days.

(21) Appl. No.: 12/785,625

(22) Filed: May 24, 2010

(65) Prior Publication Data

US 2010/0234331 A1    Sep. 16, 2010

Related U.S. Application Data

(62) Division of application No. 11/525,573, filed on Sep. 22, 2006, now Pat. No. 7,851,498.

(60) Provisional application No. 60/719,884, filed on Sep. 23, 2005.

(51) Int. Cl.
| | |
|---|---|
| *A61K 31/56* | (2006.01) |
| *A61K 31/416* | (2006.01) |
| *A61K 31/454* | (2006.01) |
| *A61P 3/10* | (2006.01) |

(52) U.S. Cl. ........ 514/170; 514/171; 514/217; 514/242; 514/322; 514/391; 514/406

(58) Field of Classification Search ................. None
See application file for complete search history.

(56) References Cited

U.S. PATENT DOCUMENTS

2005/0228034 A1 * 10/2005 Lagu et al. ............... 514/406
* cited by examiner

*Primary Examiner* — Kamal Saeed
(74) *Attorney, Agent, or Firm* — Thomas J. Dodd

(57) ABSTRACT

This invention is directed to a hexahydro-cyclooctyl pyrazole cannabinoid modulator compound of formula (I):

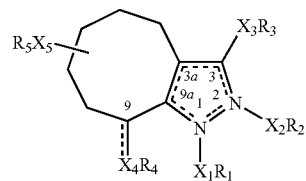

and a method for use in treating, ameliorating or preventing a cannabinoid receptor mediated syndrome, disorder or disease.

10 Claims, No Drawings

HEXAHYDRO-CYCLOOCTYL PYRAZOLE CANNABINOID MODULATORS

CROSS REFERENCE TO RELATED APPLICATIONS

The present application is a divisional application of U.S. application Ser. No. 11/525,573 filed Sep. 22, 2006 now U.S. Pat. No. 7,851,498 which claims the benefits of the filing of U.S. Provisional Application No. 60/719,884, filed Sep. 23, 2005. The complete disclosures of the aforementioned related patent applications are hereby incorporated herein by reference for all purposes.

FIELD OF THE INVENTION

This invention is directed to hexahydro-cyclooctyl pyrazole cannabinoid (CB) modulator compounds and a method for use in treating, ameliorating or preventing a cannabinoid receptor mediated syndrome, disorder or disease.

BACKGROUND OF THE INVENTION

Before the discovery of the cannabinoid CB1 and CB2 receptors, the term cannabinoid was used to describe the biologically active components of *cannabis sativa*, the most abundant of which are delta-9-tetrahydrocannabinol (THC) and cannabidiol.

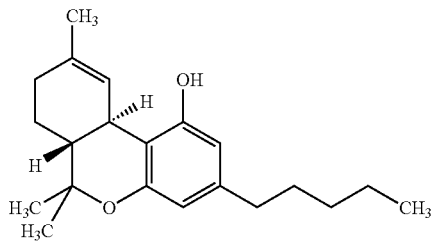

THC

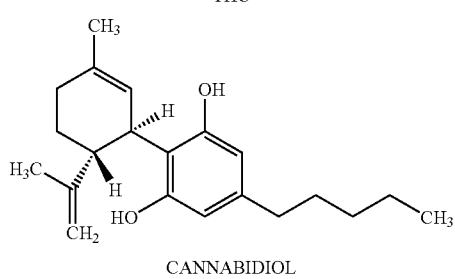

CANNABIDIOL

THC is a moderately potent partial agonist of the CB1 and CB2 receptors and is considered the "classical cannabinoid," a term now used to refer to other analogues and derivatives that are structurally related to the tricyclic dibenzopyran THC core. The term "nonclassical cannabinoid" refers to cannabinoid agonists structurally related to cannabidiol.

Pharmacological investigations have concentrated on selective CB receptor modulators of the pyrazole structural class, which include SR 141716A (the monohydrochloride salt of SR 141716) and SR 144528.

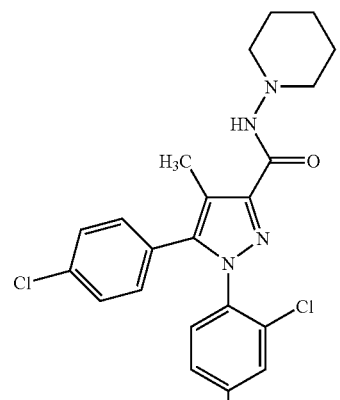

SR 141716

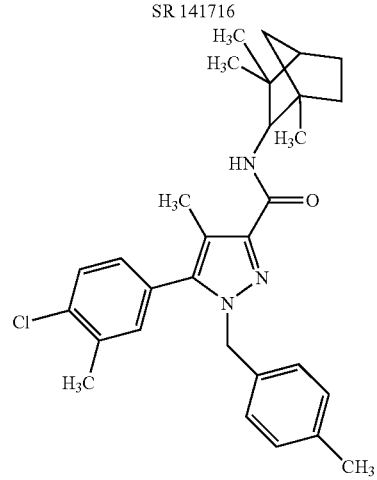

SR 144528

Pyrazole cannabinoid modulators are one among the many different structural classes which have aided the development of CB pharmacology, have helped to determine the biological effects mediated by the cannabinoid receptors, will lead to further refinement of current compounds and will be a source of new chemical classes in the future.

Certain compounds (including SR 141716, SR 144528 and the like) that were originally classified as selective antagonists are now considered to act as "inverse agonists" rather than pure antagonists. Inverse agonists have the ability to decrease the constitutive level of receptor activation in the absence of an agonist instead of only blocking the activation induced by agonist binding at the receptor. The constitutive activity of CB receptors has important implications since there is a level of continuous signaling by both CB1 and CB2 even in the absence of an agonist. For example, SR 141716A increases CB1 protein levels and sensitizes cells toward agonist action, thus indicating that inverse agonists may be another class of ligands used to modulate the endocannabinoid system and the downstream signaling pathways activated by CB receptors.

PCT Application WO2006/030124 describes pyrazole derivatives as CB1 or CB2 receptor agonists.

Advances in the synthesis of CB and cannabimimetic ligands have furthered the development of receptor pharmacology and provided evidence for the existence of additional cannabinoid receptor sub-types. However, there remains an ongoing need for the identification and development of CB1 or CB2 receptor cannabinoid modulators for the treatment of a variety of CB receptor modulated syndromes, disorders and diseases.

DETAILED DESCRIPTION OF THE INVENTION

This invention is directed to a compound of formula (I):

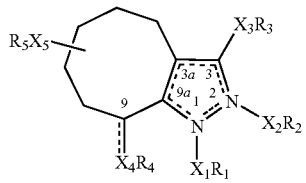

or a salt, isomer, prodrug, metabolite or polymorph thereof wherein the dashed lines between positions 2-3 and positions 3a-9a in formula (I) represent locations for each of two double bonds present when $X_1R_1$ is present;

the dashed lines between positions 3-3a and positions 9a-1 in formula (I) represent locations for each of two double bonds present when $X_2R_2$ is present;

the dashed line between position 9 and $X_4R_4$ in formula (I) represents the location for a double bond;

$X_1$ is absent or lower alkylene;

$X_2$ is absent or lower alkylene;

wherein only one of $X_1R_1$ and $X_2R_2$ are present;

$X_3$ is absent, lower alkylene, lower alkylidene or —NH—;

when the dashed line between position 9 and $X_4R_4$ is absent, $X_4$ is absent or lower alkylene;

when the dashed line between position 9 and $X_4R_4$ is present, $X_4$ is absent;

$X_5$ is absent or lower alkylene;

$R_1$ is selected from hydrogen, alkyl (optionally substituted at one or more positions by halogen, hydroxy or lower alkoxy), lower alkyl-sulfonyl, aryl, $C_3$-$C_{12}$ cycloalkyl or heterocyclyl, wherein aryl, $C_3$-$C_{12}$ cycloalkyl or heterocyclyl is each optionally substituted at one or more positions by halogen, aminosulfonyl, lower alkyl-aminosulfonyl, alkyl (optionally substituted at one or more positions by halogen, hydroxy or lower alkoxy), hydroxy or alkoxy (optionally substituted at one or more positions by halogen or hydroxy);

$R_2$ is selected from hydrogen, alkyl (optionally substituted at one or more positions by halogen, hydroxy or lower alkoxy), lower alkyl-sulfonyl, aryl, $C_3$-$C_{12}$ cycloalkyl or heterocyclyl, wherein aryl, $C_3$-$C_{12}$ cycloalkyl or heterocyclyl is each optionally substituted at one or more positions by halogen, aminosulfonyl, lower alkyl-aminosulfonyl, alkyl (optionally substituted at one or more positions by halogen, hydroxy or lower alkoxy), hydroxy or alkoxy (optionally substituted at one or more positions by halogen or hydroxy);

$R_3$ is —C(O)—$Z_1$($R_6$), —$SO_2$—$NR_7$—$Z_2$($R_8$) or —C(O)—$NR_9$—$Z_3$($R_{10}$);

when the dashed line between position 9 and $X_4R_4$ is absent, $X_4$ is absent or lower alkylene and $R_4$ is hydrogen, hydroxy, lower alkyl, lower alkoxy, halogen, aryl, $C_3$-$C_{12}$ cycloalkyl or heterocyclyl, wherein aryl, $C_3$-$C_{12}$ cycloalkyl or heterocyclyl is each optionally substituted at one or more positions by hydroxy, oxo, lower alkyl (optionally substituted at one or more positions by halogen, hydroxy or lower alkoxy), lower alkoxy (optionally substituted at one or more positions by halogen or hydroxy) or halogen;

when the dashed line between position 9 and $X_4R_4$ is present, $X_4$ is absent and $R_4$ is CH-aryl or CH-heterocyclyl, wherein aryl or heterocyclyl is each optionally substituted at one or more positions by hydroxy, oxo, lower alkyl, lower alkoxy or halogen;

$R_5$ is absent, hydroxy, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl;

$R_6$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl;

$R_7$ is hydrogen or lower alkyl;

$R_8$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl;

$R_9$ is hydrogen or lower alkyl;

$R_{10}$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aminosulfonyl, lower alkyl-aminosulfonyl, aryl, aryloxy, arylalkoxy or heterocyclyl;

$Z_1$ and $Z_2$ is each absent or alkyl; and, $Z_3$ is absent, —NH—, —$SO_2$— or alkyl (wherein alkyl is optionally substituted at one or more positions by halogen, hydroxy, lower alkyl, lower alkoxy, carboxy or carbonylalkoxy).

An example of the present invention is a compound of formula (I) or a salt, isomer, prodrug, metabolite or polymorph thereof wherein $X_1$ is absent or lower alkylene; and, $R_1$ is selected from hydrogen, alkyl (optionally substituted at one or more positions by halogen, hydroxy or lower alkoxy), aryl, $C_3$-$C_{12}$ cycloalkyl or heterocyclyl, wherein aryl, $C_3$-$C_{12}$ cycloalkyl or heterocyclyl is each optionally substituted at one or more positions by halogen, alkyl (optionally substituted at one or more positions by halogen, hydroxy or lower alkoxy), hydroxy or alkoxy (optionally substituted at one or more positions by halogen or hydroxy).

An example of the present invention is a compound of formula (I) or a salt, isomer, prodrug, metabolite or polymorph thereof wherein $X_1$ is absent; and, $R_1$ is selected from aryl or $C_3$-$C_{12}$ cycloalkyl, wherein aryl is optionally substituted at one or more positions by halogen.

An example of the present invention is a compound of formula (I) or a salt, isomer, prodrug, metabolite or polymorph thereof wherein $R_3$ is —C(O)—$Z_1$($R_6$), —$SO_2$—NH—$Z_2$($R_8$) or —C(O)—NH—$Z_3$($R_{10}$).

An example of the present invention is a compound of formula (I) or a salt, isomer, prodrug, metabolite or polymorph thereof wherein $R_3$ is —C(O)—$Z_1$($R_6$); $X_3$ is absent, lower alkylene, lower alkylidene or —NH—; $Z_1$ is absent or alkyl; and, $R_6$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl.

An example of the present invention is a compound of formula (I) or a salt, isomer, prodrug, metabolite or polymorph thereof wherein $R_3$ is —C(O)—$Z_1$($R_6$); $X_3$ is absent; $Z_1$ is absent; and, $R_6$ is heterocyclyl.

An example of the present invention is a compound of formula (I) or a salt, isomer, prodrug, metabolite or polymorph thereof wherein $R_3$ is —C(O)—$NR_9$—$Z_3$($R_{10}$); $X_3$ is absent, lower alkylene, lower alkylidene or —NH—; $R_9$ is hydrogen or lower alkyl; $Z_3$ is absent, —NH—, —$SO_2$— or alkyl (wherein alkyl is optionally substituted at one or more positions by halogen, hydroxy, lower alkyl, lower alkoxy, carboxy or carbonylalkoxy); and, $R_{10}$ is aryl, $C_3$-$C_{12}$ cycloalkyl or heterocyclyl each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aminosulfonyl, lower alkyl-aminosulfonyl, aryl, aryloxy, arylalkoxy or heterocyclyl.

An example of the present invention is a compound of formula (I) or a salt, isomer, prodrug, metabolite or polymorph thereof wherein $R_3$ is —C(O)—NH—$Z_3$($R_{10}$); $X_3$ is absent; $Z_3$ is absent, —NH— or alkyl (wherein alkyl is optionally substituted at one or more positions by halogen, hydroxy, lower alkyl, lower alkoxy, carboxy or carbonylalkoxy); and, $R_{10}$ is aryl, $C_3$-$C_{12}$ cycloalkyl or heterocyclyl each optionally substituted by one or more hydroxy, oxo, halogen, amino, aminoalkyl, alkyl (optionally substituted at one or more positions by halogen, hydroxy or lower alkoxy), alkoxy, carboxy, carbonylalkoxy, aryl or heterocyclyl.

An example of the present invention is a compound of formula (I) or a salt, isomer, prodrug, metabolite or polymorph thereof wherein $R_3$ is —C(O)—NH—$Z_3$($R_{10}$); $X_3$ is absent; $Z_3$ is absent or alkyl; and, $R_{10}$ is $C_3$-$C_{12}$ cycloalkyl optionally substituted by one or more hydroxy, oxo, halogen, amino, aminoalkyl, alkyl (optionally substituted at one or more positions by halogen, hydroxy or lower alkoxy), alkoxy, carboxy, carbonylalkoxy, aryl or heterocyclyl.

An example of the present invention is a compound of formula (I) or a salt, isomer, prodrug, metabolite or polymorph thereof wherein $R_3$ is —C(O)—NH—$Z_3$($R_{10}$); $X_3$ is absent; $Z_3$ is absent or alkyl; and, $R_{10}$ is $C_3$-$C_{12}$ cycloalkyl optionally substituted by one or more alkyl or carbonylalkoxy.

An example of the present invention is a compound of formula (I) or a salt, isomer, prodrug, metabolite or polymorph thereof wherein $R_3$ is —C(O)—NH—$Z_3$($R_{10}$); $X_3$ is absent; $Z_3$ is absent, —NH— or alkyl (wherein alkyl is optionally substituted at one or more positions by halogen, hydroxy, lower alkyl, lower alkoxy, carboxy or carbonylalkoxy); and, $R_{10}$ is aryl optionally substituted by one or more hydroxy, oxo, halogen, amino, aminoalkyl, alkyl (optionally substituted at one or more positions by halogen, hydroxy or lower alkoxy), alkoxy, carboxy, carbonylalkoxy, aryl or heterocyclyl.

An example of the present invention is a compound of formula (I) or a salt, isomer, prodrug, metabolite or polymorph thereof wherein $R_3$ is —C(O)—NH—$Z_3$($R_{10}$); $X_3$ is absent; $Z_3$ is absent, —NH— or alkyl; and, $R_{10}$ is aryl optionally substituted by one or more halogen.

An example of the present invention is a compound of formula (I) or a salt, isomer, prodrug, metabolite or polymorph thereof wherein $R_3$ is —C(O)—NH—$Z_3$($R_{10}$); $X_3$ is absent; $Z_3$ is absent or alkyl (wherein alkyl is optionally substituted at one or more positions by halogen, hydroxy, lower alkyl, lower alkoxy, carboxy or carbonylalkoxy); and, $R_{10}$ is heterocyclyl optionally substituted by one or more alkyl.

An example of the present invention is a compound of formula (I) or a salt, isomer, prodrug, metabolite or polymorph thereof wherein the dashed line between position 9 and $X_4R_4$ is absent; $X_4$ is absent; and, $R_4$ is hydrogen.

An example of the present invention is a compound of formula (I) or a salt, isomer, prodrug, metabolite or polymorph thereof wherein the dashed line between position 9 and $X_4R_4$ is present, $X_4$ is absent and $R_4$ is CH-aryl optionally substituted on aryl at one or more positions by halogen.

An example of the present invention is a compound of formula (I) or a salt, isomer, prodrug, metabolite or polymorph thereof wherein $X_5$ is absent and $R_5$ is absent.

An example of the present invention is a compound of formula (Ia):

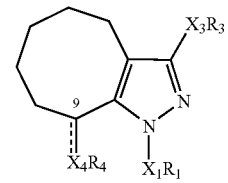

or a salt, isomer, prodrug, metabolite or polymorph thereof wherein $X_1$ is absent; $X_3$ is absent; when the dashed line between position 9 and $X_4R_4$ is absent, $X_4$ is absent and $R_4$ is hydrogen; when the dashed line between position 9 and $X_4R_4$ is present, $X_4$ is absent and $R_4$ is CH-aryl, wherein aryl is optionally substituted at one or more positions by halogen; $R_1$ is selected from aryl or $C_3$-$C_{12}$ cycloalkyl, wherein aryl is optionally substituted at one or more positions by halogen; $R_3$ is —C(O)—$Z_1$($R_6$) or —C(O)—NH—$Z_3$($R_{10}$); $R_6$ is heterocyclyl; $R_{10}$ is aryl, $C_3$-$C_{12}$ cycloalkyl or heterocyclyl, wherein aryl or $C_3$-$C_{12}$ cycloalkyl is each optionally substituted by one or more halogen, alkyl or carbonylalkoxy; $Z_1$ is absent; and, $Z_3$ is absent, —NH— or alkyl.

An example of the present invention is a compound of formula (Ia) or a salt, isomer, prodrug, metabolite or polymorph thereof wherein $X_1R_1$, $X_3R_3$ and $X_4R_4$ are dependently selected from

| Cpd | $X_1R_1$ | $X_3R_3$ | $X_4R_4$ |
|---|---|---|---|
| 1 | cyclohexyl | C(O)NH-1,3,3-$(CH_3)_3$-bicyclo[2.2.1]hept-2-yl | H |
| 2 | cyclohexyl | C(O)NH—$CH_2$-adamantan-1-yl | H |
| 3 | cyclopentyl | C(O)NH—$CH_2$-adamantan-1-yl | H |
| 4 | cyclohexyl | C(O)NH-2-$CO_2CH_2CH_3$-bicyclo[2.2.1]hept-2-yl | H |

-continued

| Cpd | $X_1R_1$ | $X_3R_3$ | $X_4R_4$ |
|---|---|---|---|
| 5 | cyclopentyl | C(O)NH—CH(CH$_3$)-adamantan-1-yl | H |
| 6 | cyclohexyl | C(O)NH—CH(CH$_3$)-adamantan-1-yl | H |
| 7 | cyclopentyl | C(O)NH-1,3,3-(CH$_3$)$_3$-bicyclo[2.2.1]hept-2-yl | H |
| 8 | cyclobutyl | C(O)NH-1,3,3-(CH$_3$)$_3$-bicyclo[2.2.1]hept-2-yl | H |
| 9 | cyclobutyl | C(O)NH—CH$_2$-adamantan-1-yl | H |
| 10 | cyclobutyl | C(O)NH—CH(CH$_3$)-adamantan-1-yl | H |
| 11 | 2,4-Cl$_2$-phenyl | C(O)NHNH-(2,4-Cl$_2$)-phenyl | (E)-4-F-benzylidene |
| 12 | 2,4-Cl$_2$-phenyl | C(O)NH—(R—CH)(phenyl)-CH$_3$ | (E)-4-F-benzylidene |
| 13 | 2,4-Cl$_2$-phenyl | C(O)NH—(R—CH)(pyridin-2-yl)-CH$_3$ | (E)-4-F-benzylidene |
| 14 | 2,4-Cl$_2$-phenyl | C(O)-piperidin-1-yl | (E)-4-F-benzylidene |
| 15 | 2,4-Cl$_2$-phenyl | C(O)NH—(S—CH)(phenyl)-CH$_3$ | (E)-4-F-benzylidene |
| 16 | 2,4-Cl$_2$-phenyl | C(O)NH—(S—CH)(cyclohexyl)-CH$_3$ | (E)-4-F-benzylidene |
| 17 | 2,4-Cl$_2$-phenyl | C(O)NH—(R—CH)(cyclohexyl)-CH$_3$ | (E)-4-F-benzylidene |
| 18 | 2,4-Cl$_2$-phenyl | C(O)NH-hexahydrocyclopenta[c]pyrrol-2-yl | (E)-4-F-benzylidene |
| 19 | 2,4-Cl$_2$-phenyl | C(O)NH-piperidin-1-yl | (E)-4-F-benzylidene |

Compounds of Formula (I) and pharmaceutically acceptable forms thereof include those selected from:

Cpd 1

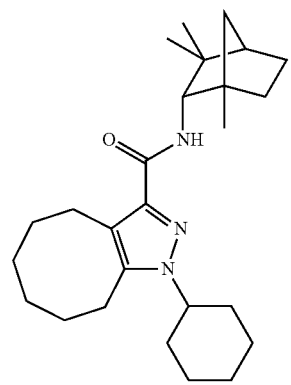

Cpd 2

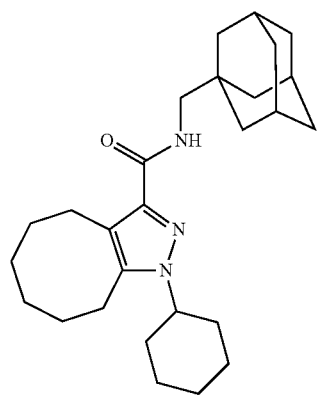

Cpd 3

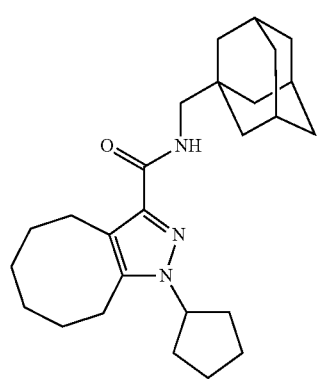

Cpd 4

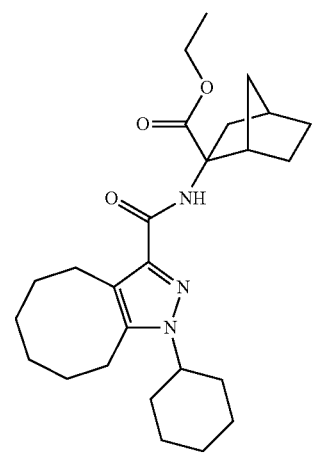

Cpd 5

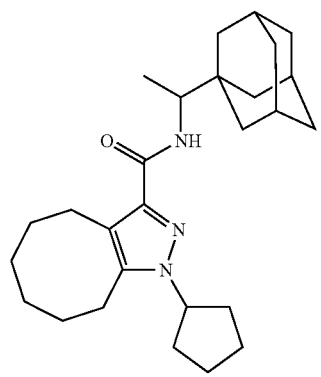

Cpd 6
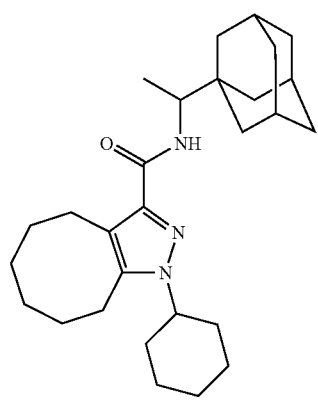
Cpd 7
Cpd 8
Cpd 9
Cpd 10
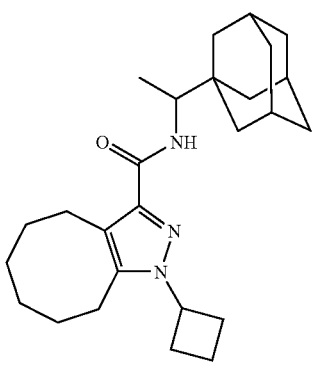
Cpd 11
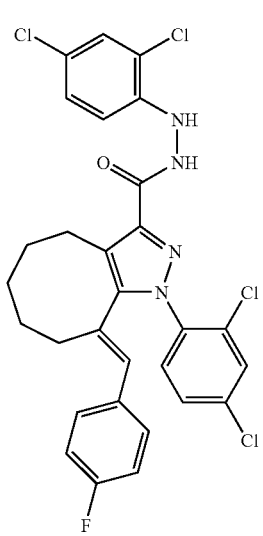
Cpd 12
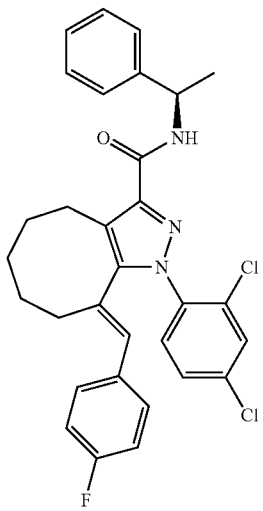

Cpd 13
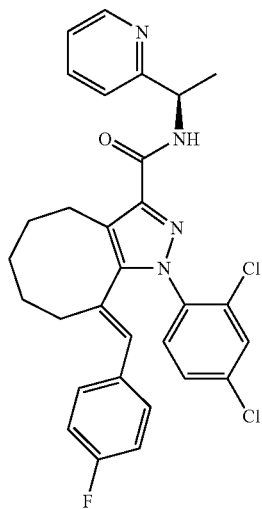
Cpd 14
Cpd 16
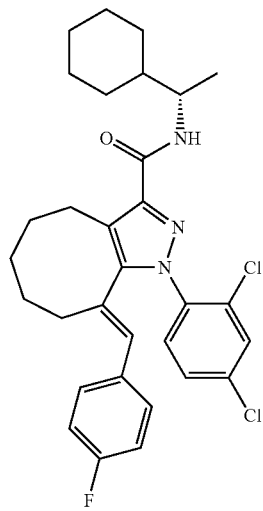
Cpd 17
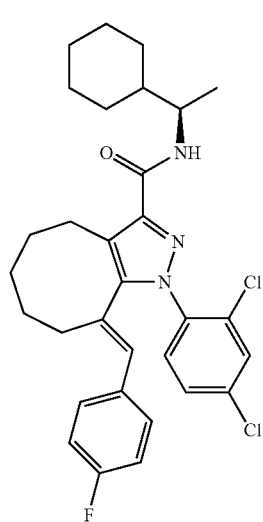
Cpd 15
Cpd 18
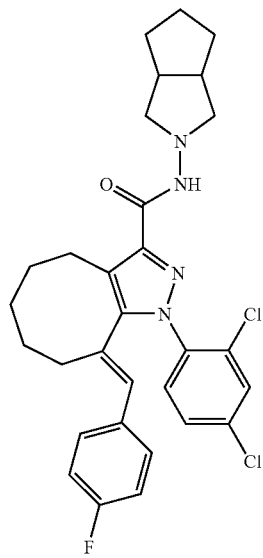

Cpd 19

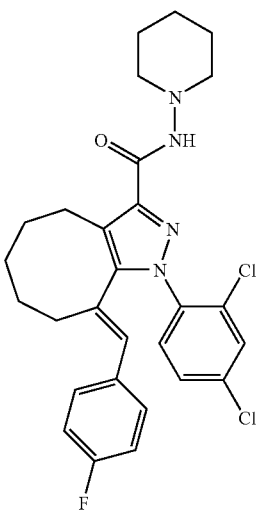

DEFINITIONS

As used herein, the following terms have the following meanings:

The term "alkyl" means a saturated branched or straight chain monovalent hydrocarbon radical of up to 10 carbon atoms. Alkyl typically includes, but is not limited to, methyl, ethyl, propyl, isopropyl, n-butyl, t-butyl, pentyl, hexyl, heptyl and the like.

The term "lower alkyl" means an alkyl radical of up to 4 carbon atoms. The point of attachment may be on any alkyl or lower alkyl carbon atom and, when further substituted, substituent variables may be placed on any carbon atom.

The term "alkylene" means a saturated branched or straight chain monovalent hydrocarbon linking group of up to 10 carbon atoms, whereby the linking group is derived by the removal of one hydrogen atom each from two carbon atoms. Alkylene typically includes, but is not limited to, methylene, ethylene, propylene, isopropylene, n-butylene, t-butylene, pentylene, hexylene, heptylene and the like. The term "lower alkylene" means an alkylene linking group of up to 4 carbon atoms. The point of attachment may be on any alkylene or lower alkylene carbon atom and, when further substituted, substituent variables may be placed on any carbon atom.

The term "alkylidene" means an alkylene linking group of from 1 to 10 carbon atoms having at least one double bond formed between two adjacent carbon atoms, wherein the double bond is derived by the removal of one hydrogen atom each from the two carbon atoms. Atoms may be oriented about the double bond in either the cis (E) or trans (Z) conformation. Alkylidene typically includes, but is not limited to, methylidene, vinylidene, propylidene, iso-propylidene, methallylene, allylidene (2-propenylidene), crotylene (2-butenylene), prenylene (3-methyl-2-butenylene) and the like. The term "lower alkylidene" means a radical or linking group of from 1 to 4 carbon atoms. The point of attachment may be on any alkylidene or lower alkylidene carbon atom and, when further substituted, substituent variables may be placed on any carbon atom.

The term "alkoxy" means an alkyl, alkylene or alkylidene radical of up to 10 carbon atoms attached via an oxygen atom, whereby the point of attachment is formed by the removal of the hydrogen atom from a hydroxide substituent on a parent radical. The term "lower alkoxy" means an alkyl, alkylene or alkylidene radical of up to 4 carbon atoms. Lower alkoxy typically includes, but is not limited to, methoxy, ethoxy, propoxy, butoxy and the like. When further substituted, substituent variables may be placed on any alkoxy carbon atom.

The term "cycloalkyl" means a saturated or partially unsaturated monocyclic, polycyclic or bridged hydrocarbon ring system radical or linking group. A ring of 3 to 20 carbon atoms may be designated by $C_{3-20}$ cycloalkyl; a ring of 3 to 12 carbon atoms may be designated by $C_{3-12}$ cycloalkyl, a ring of 3 to 8 carbon atoms may be designated by $C_{3-8}$ cycloalkyl and the like.

Cycloalkyl typically includes, but is not limited to, cyclopropyl, cyclobutyl, cyclopentyl, cyclohexyl, cyclohexenyl, cycloheptyl, cyclooctyl, indanyl, indenyl, 1,2,3,4-tetrahydro-naphthalenyl, 5,6,7,8-tetrahydro-naphthalenyl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1]octyl, bicyclo[2.2.2]octenyl, bicyclo[3.2.1]octenyl, adamantanyl, octahydro-4,7-methano-1H-indenyl, octahydro-2,5-methano-pentalenyl (also referred to as hexahydro-2,5-methano-pentalenyl) and the like. When further substituted, substituent variables may be placed on any ring carbon atom.

The term "heterocyclyl" means a saturated, partially unsaturated or unsaturated monocyclic, polycyclic or bridged hydrocarbon ring system radical or linking group, wherein at least one ring carbon atom has been replaced with one or more heteroatoms independently selected from N, O or S. A heterocyclyl ring system further includes a ring system having up to 4 nitrogen atom ring members or a ring system having from 0 to 3 nitrogen atom ring members and 1 oxygen or sulfur atom ring member. When allowed by available valences, up to two adjacent ring members may be a heteroatom, wherein one heteroatom is nitrogen and the other is selected from N, O or S. A heterocyclyl radical is derived by the removal of one hydrogen atom from a single carbon or nitrogen ring atom. A heterocyclyl linking group is derived by the removal of two hydrogen atoms each from either carbon or nitrogen ring atoms.

Heterocyclyl typically includes, but is not limited to, furyl, thienyl, 2H-pyrrole, 2-pyrrolinyl, 3-pyrrolinyl, pyrrolidinyl, pyrrolyl, 1,3-dioxolanyl, oxazolyl, thiazolyl, imidazolyl, 2-imidazolinyl (also referred to as 4,5-dihydro-1H-imidazolyl), imidazolidinyl, 2-pyrazolinyl, pyrazolidinyl, pyrazolyl, isoxazolyl, isothiazolyl, oxadiazolyl, triazolyl, thiadiazolyl, tetrazolyl, 2H-pyran, 4H-pyran, pyridinyl, piperidinyl, 1,4-dioxanyl, morpholinyl, 1,4-dithianyl, thiomorpholinyl, pyridazinyl, pyrimidinyl, pyrazinyl, piperazinyl, azepanyl, indolizinyl, indolyl, isoindolyl, 3H-indolyl, indolinyl, benzo[b]furyl, benzo[b]thienyl, 1H-indazolyl, benzimidazolyl, benzthiazolyl, purinyl, 4H-quinolizinyl, quinolinyl, iso-quinolinyl, cinnolinyl, phthalzinyl, quinazolinyl, quinoxalinyl, 1,8-naphthyridinyl, pteridinyl, quinuclidinyl, hexahydro-1,4-diazepinyl, 1,3-benzodioxolyl (also known as 1,3-methylenedioxyphenyl), 2,3-dihydro-1,4-benzodioxinyl (also known as 1,4-ethylenedioxyphenyl), benzo-dihydro-furyl, benzo-tetrahydro-pyranyl, benzo-dihydro-thienyl, 5,6,7,8-tetrahydro-4H-cyclohepta(b)thienyl, 5,6,7-trihydro-4H-cyclohexa(b)thienyl, 5,6-dihydro-4H-cyclopenta(b)thienyl, 2-aza-bicyclo[2.2.1]heptyl, 1-aza-bicyclo[2.2.2]octyl, 8-aza-bicyclo[3.2.1]octyl, 7-oxa-bicyclo[2.2.1]heptyl and the like.

The term "aryl" means an unsaturated, conjugated 7E electron monocyclic or polycyclic hydrocarbon ring system radical or linking group of 6, 9, 10 or 14 carbon atoms. An aryl radical is derived by the removal of one hydrogen atom from a single carbon ring atom. An arylene linking group is derived by the removal of two hydrogen atoms each of two carbon ring atoms. Aryl typically includes, but is not limited to, phenyl, naphthalenyl, azulenyl, anthracenyl and the like.

The term "amino" means a radical of the formula or —$NH_2$.

The term "aminoalkyl" means a radical of the formula —NH-alkyl or —N(alkyl)$_2$.

The term "aminosulfonyl" means a radical of the formula or —$SO_2NH_2$.

The term "arylalkoxy" means a radical of the formula —O-alkyl-aryl.

The term "aryloxy" means a radical of the formula —O-aryl.

The term "carbamoyl" means a radical of the formula or —C(O)$NH_2$.

The term "carbamoylalkyl" means a radical of the formula —C(O)NH-alkyl or —C(O)N(alkyl)$_2$.

The term "carbonylalkoxy" means a radical of the formula —C(O)O-alkyl.

The term "carboxy" means a radical of the formula —COOH or —$CO_2H$.

The term "halo" or "halogen" means fluoro, chloro, bromo or iodo.

The term "lower alkyl-amino" means a radical of the formula —NH-alkyl or —N(alkyl)$_2$.

The term "lower alkyl-aminosulfonyl" means a radical of the formula —$SO_2$NH-alkyl or —$SO_2$N(alkyl)$_2$.

The term "lower alkyl-sulfonyl" means a radical of the formula —$SO_2$-alkyl or —C(O)N(alkyl)$_2$.

The term "substituted" means one or more hydrogen atoms on a core molecule have been replaced with one or more radicals or linking groups, wherein the linking group, by definition is also further substituted. The ability of a particular radical or linking group to replace a hydrogen atom is optimally expected by one skilled to art to result in a chemically stable core molecule.

The term "dependently selected" means one or more substituent variables are present in a specified combination (e.g. groups of substituents commonly appearing in a tabular list).

The substituent nomenclature used in the disclosure of the present invention was derived using nomenclature rules well known to those skilled in the art (e.g., IUPAC).

Pharmaceutical Forms

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphosulfonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The present invention includes within its scope prodrugs and metabolites of the compounds of this invention. In general, such prodrugs and metabolites will be functional derivatives of the compounds that are readily convertible in vivo into an active compound.

Thus, in the methods of treatment of the present invention, the term "administering" shall encompass the means for treating, ameliorating or preventing a syndrome, disorder or disease described herein with a compound specifically disclosed or a compound, or prodrug or metabolite thereof, which would obviously be included within the scope of the invention albeit not specifically disclosed for certain of the instant compounds.

The term "prodrug" means a pharmaceutically acceptable form of a functional derivative of a compound of the invention (or a salt thereof), wherein the prodrug may be: 1) a relatively active precursor which converts in vivo to an active prodrug component; 2) a relatively inactive precursor which converts in vivo to an active prodrug component; or 3) a relatively less active component of the compound that contributes to therapeutic biological activity after becoming available in vivo (i.e., as a metabolite). Conventional procedures for the selection and preparation of suitable prodrug derivatives are described in, for example, "*Design of Prodrugs*", ed. H. Bundgaard, Elsevier, 1985.

The term "metabolite" means a pharmaceutically acceptable form of a metabolic derivative of a compound of the invention (or a salt thereof), wherein the derivative is a relatively less active component of the compound that contributes to therapeutic biological activity after becoming available in vivo.

The present invention contemplates compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "stereoisomer" refers to isomers of identical constitution that differ in the arrangement of their atoms in space. Enantiomers and diastereomers are stereoisomers wherein an asymmetrically substituted carbon atom acts as a chiral center. The term "chiral" refers to a molecule that is not superposable on its mirror image, implying the absence of an axis and a plane or center of symmetry. The term "enantiomer" refers to one of a pair of molecular species that are mirror images of each other and are not superposable. The term "diastereomer" refers to stereoisomers that are not related as mirror images. The symbols "R" and "S" represent the configuration of substituents around a chiral carbon atom(s). The symbols "R*" and "S*" denote the relative configurations of substituents around a chiral carbon atom(s).

The term "racemate" or "racemic mixture" refers to a compound of equimolar quantities of two enantiomeric species, wherein the compound is devoid of optical activity. The term "optical activity" refers to the degree to which a chiral molecule or nonracemic mixture of chiral molecules rotates the plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) or "chair" configuration, the substituents are on opposite sides in relationship to the carbon-carbon double bond; in the "Z" (same sided) or "boat" configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans". Substituent atoms (other than H) attached to a bridged bicyclic system may be in an "endo" or "exo" configuration. In the "endo" configuration, the substituents attached to a bridge (not a bridgehead) point toward the larger of the two remaining bridges; in the "exo" configuration, the substituents attached to a bridge point toward the smaller of the two remaining bridges.

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "S*," "R*," "E," "Z," "cis," "trans," "exo" and "endo" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC column.

Furthermore, compounds of the present invention may have one or more polymorph or amorphous crystalline forms and as such are intended to be included in the scope of the invention. In addition, some of the compounds may form solvates with water (i.e., hydrates) or common organic solvents, and such are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known in the art.

Therapeutic Use

CB1 and CB2 cannabinoid receptors belong to the G-protein-coupled receptor (GCPR) family, a receptor super-family with a distinctive pattern of seven transmembrane domains, which inhibits N-type calcium channels and/or adenylate cyclase to inhibit Q-type calcium channels. CB1 receptors are present in the CNS, predominately expressed in brain regions associated with memory and movement such as the hippocampus (memory storage), cerebellum (coordination of motor function, posture and balance), basal ganglia (movement control), hypothalamus (thermal regulation, neuroendocrine release, appetite), spinal cord (nociception), cerebral cortex (emesis) and periphery regions such as lymphoid organs (cell mediated and innate immunity), vascular smooth muscle cells (blood pressure), gastrointestinal tract (innate antiinflammatory in the tract and in the esophagus, duodenum, jejunum, ileum and colon, controlling esophageal and gastrointestinal motility), lung smooth muscle cells (bronchodilation), eye ciliary body (intraocular pressure).

CB2 receptors appear to be primarily expressed peripherally in lymphoid tissue (cell mediated and innate immunity), peripheral nerve terminals (peripheral nervous system), spleen immune cells (immune system modulation) and retina (intraocular pressure). CB2 mRNA is found in the CNS in cerebellar granule cells (coordinating motor function). Pharmacological and physiological evidence also suggests that there may be other cannabinoid receptor subtypes that have yet to be cloned and characterized.

Where activation or inhibition of a CB receptor appears to mediate various syndromes, disorders or diseases, potential areas of clinical application include, but are not limited to, controlling appetite, regulating metabolism, diabetes, reducing glaucoma-associated intraocular pressure, treating social and mood disorders, treating seizure-related disorders, treating substance abuse disorders, enhancing learning, cognition and memory, controlling organ contraction and muscle spasm, treating bowel disorders, treating respiratory disorders, treating locomotor activity or movement disorders, treating immune and inflammation disorders, regulating cell growth, use in pain management, use as a neuroprotective agent and the like.

Thus, cannabinoid receptor modulators, including the compounds of the formula (I) or (Ia) of the present invention, are useful for treating, ameliorating or preventing a cannabinoid receptor mediated syndrome, disorder or disease including, but not limited to, controlling appetite, regulating metabolism, diabetes, glaucoma-associated intraocular pressure, pain, social and mood disorders, seizure-related disorders, substance abuse disorders, learning, cognition and/or memory disorders, bowel disorders, respiratory disorders, locomotor activity disorders, movement disorders, immune disorders or inflammation disorders, controlling organ contraction and muscle spasm, enhancing learning, cognition and/or memory, regulating cell growth, providing neuroprotection and the like.

The present invention is directed to a method for treating, ameliorating or preventing a cannabinoid receptor mediated syndrome, disorder or disease in a subject in need thereof comprising the step of administering to the subject an effective amount of a compound of formula (I).

The present invention is directed to a method for treating, ameliorating or preventing a cannabinoid receptor mediated syndrome, disorder or disease in a subject in need thereof comprising the step of administering to the subject an effective amount of a compound of formulae (Ia) or prodrug, metabolite, or composition thereof.

The present invention is directed to a method for treating, ameliorating or preventing a cannabinoid receptor mediated syndrome, disorder or disease in a subject in need thereof comprising the step of administering to the subject a combination product and/or therapy comprising an effective amount of a compound of formula (I) and a therapeutic agent.

The present invention is directed to a method for treating, ameliorating or preventing a cannabinoid receptor mediated syndrome, disorder or disease in a subject in need thereof comprising the step of administering to the subject a combination product and/or therapy comprising an effective amount of a compound of formulae (Ia) and a therapeutic agent.

Therapeutic agents contemplated for use in a combination product and/or therapies of the present invention include an anticonvulsant or a contraceptive agent. The anticonvulsant agents include, and are not limited to, topiramate, analogs of topiramate, carbamazepine, valproic acid, lamotrigine, gabapentin, phenyloin and the like and mixtures or pharmaceutically acceptable salts thereof. The contraceptive agents include, and are not limited to, such as progestin-only contraceptives and contraceptives that include both a progestin component and an estrogen component. The invention further includes a pharmaceutical composition wherein the contraceptive is an oral contraceptive, and wherein the contraceptive optionally includes a folic acid component.

The invention also includes a method of contraception in a subject comprising the step of administering to the subject a composition, wherein the composition comprises a contraceptive and a CB1 receptor inverse-agonist or antagonist compound of formulae (I) or (Ia), wherein the composition reduces the urge to smoke in the subject and/or assists the subject in losing weight.

The present invention includes cannabinoid receptor modulators useful for treating, ameliorating or preventing a CB receptor mediated syndrome, disorder or disease. The usefulness of a compound of the present invention or composition thereof as a CB modulator can be determined according to the methods disclosed herein. The scope of such use includes treating, ameliorating or preventing a plurality of CB receptor mediated syndromes, disorders or diseases.

The present invention is also directed to a method for treating, ameliorating or preventing a CB receptor mediated syndrome, disorder or disease in a subject in need thereof wherein the syndrome, disorder or disease is related to appetite, metabolism, diabetes, glaucoma-associated intraocular pressure, social and mood disorders, seizures, substance abuse, learning, cognition or memory, organ contraction or muscle spasm, bowel disorders, respiratory disorders, locomotor activity or movement disorders, immune and inflammation disorders, unregulated cell growth, pain management, neuroprotection and the like.

A compound of formulae (I) or (Ia) for use as a CB receptor modulator includes a compound having a mean inhibition constant ($IC_{50}$) for CB receptor binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB1 agonist $IC_{50}$ for CB1 agonist binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB1 antagonist $IC_{50}$ for CB1 antagonist binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB1 inverse-agonist $IC_{50}$ for CB1 inverse-agonist binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB2 agonist $IC_{50}$ for CB2 agonist binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB2 antagonist $IC_{50}$ for CB2 antagonist binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

A compound of formulae (I) or (Ia) for use as a CB receptor modulator of the invention includes a compound having a CB2 inverse-agonist $IC_{50}$ for CB2 inverse-agonist binding activity of between about 50 μM to about 0.01 nM; between about 25 μM to about 0.01 nM; between about 15 μM to about 0.01 nM; between about 10 μM to about 0.01 nM; between about 1 μM to about 0.01 nM; between about 800 nM to about 0.01 nM; between about 200 nM to about 0.01 nM; between about 100 nM to about 0.01 nM; between about 80 nM to about 0.01 nM; between about 20 nM to about 0.01 nM; between about 10 nM to about 0.1 nM; or about 0.1 nM.

The term "cannabinoid receptor" refers to any one of the known or heretofore unknown subtypes of the class of cannabinoid receptors that may be bound by a cannabinoid modulator compound of the present invention; in particular, a cannabinoid receptor selected from the group consisting of a CB1 receptor and a CB2 receptor. The term "modulator" further refers to the use of a compound of the invention as a CB receptor agonist, antagonist or inverse-agonist.

The present invention includes a method for treating, ameliorating or preventing a CB receptor mediated syndrome, disorder or disease in a subject in need thereof comprising the step of administering to the subject an effective amount of a compound of the present invention or composition thereof, wherein the cannabinoid receptor is a CB1 or CB2 receptor; and, the compound is an agonist, antagonist or inverse-agonist of the receptor.

The present invention includes a method for treating, ameliorating or preventing a CB receptor mediated syndrome, disorder or disease in a subject in need thereof comprising the step of administering to the subject an effective amount of a compound of the present invention in a combination product and/or therapy with a therapeutic agent such as an anticonvulsant or contraceptive agent or composition thereof, wherein the cannabinoid receptor is a CB1 or CB2 receptor; and, the compound is an agonist, antagonist or inverse-agonist of the receptor.

It should be understood that contraceptive agents suitable for use in a combination product and/or therapy are not limited to oral contraceptives, but also include other commonly available contraceptives such as those that are administered transdermally, by injection or via implant.

Except as further specified, "combination product and/or therapy" means a pharmaceutical composition comprising a compound of formulae (I) or (Ia) in combination with one or more therapeutic agents. The dosages of the compound of formula (I) or (Ia) and the one or more therapeutic agents are adjusted when combined to achieve an effective amount.

The term "subject" as used herein, refers to a patient, which may be an animal, preferably a mammal, most preferably a human, which has been the object of treatment, observation or experiment and is at risk of (or susceptible to) developing a CB receptor mediated syndrome, disorder or disease.

The term "administering" is to be interpreted in accordance with the methods of the present invention. Such methods include therapeutically or prophylactically administering an effective amount of a composition or medicament of the present invention at different times during the course of a therapy or concurrently as a product in a combination form.

Prophylactic administration can occur prior to the manifestation of symptoms characteristic of a CB receptor mediated syndrome, disorder or disease such that the syndrome, disorder or disease is treated, ameliorated, prevented or otherwise delayed in its progression. The methods of the present invention are further to be understood as embracing all therapeutic or prophylactic treatment regimens used by those skilled in the art.

The term "effective amount" refers to that amount of active compound or pharmaceutical agent that elicits the biological or medicinal response in a tissue system, animal or human, that is being sought by a researcher, veterinarian, medical doctor, or other clinician, which includes alleviation of the symptoms of the syndrome, disorder or disease being treated. The effective amount of a compound of the invention is from about 0.001 mg/kg/day to about 300 mg/kg/day.

Wherein the present invention is directed to the administration of a combination of a compound of formula (I) and an anticonvulsant or contraceptive agent, the term "effective amount" means that amount of the combination of agents taken together so that the combined effect elicits the desired biological or medicinal response.

As those skilled in the art will appreciate, the effective amounts of the components comprising the combination product may be independently optimized and combined to achieve a synergistic result whereby the pathology is reduced more than it would be if the components of the combination product were used alone.

For example, the effective amount of a combination product and/or therapy comprising administration of a compound of formula (I) and topiramate would be the amount of the compound of formula (I) and the amount of topiramate that when taken together or sequentially have a combined effect that is effective. Further, it will be recognized by one skilled in the art that in the case of combination product and/or therapy with an effective amount, as in the example above, the amount of the compound of formula (I) and/or the amount of the anticonvulsant (e.g., topiramate) individually may or may not be effective.

Wherein the present invention is directed to the administration of a combination product and/or therapy, the instant compound and the anticonvulsant or contraceptive agent may be co-administered by any suitable means, simultaneously, sequentially or in a single pharmaceutical composition. Where the instant compound(s) and the anticonvulsant or contraceptive agent components are administered separately, the number of dosages of each compound(s) given per day, may not necessarily be the same, e.g. where one compound may have a greater duration of activity, and will therefore, be administered less frequently.

The compound(s) of formula (I) and the anticonvulsant(s) or contraceptive agent(s) may be administered via the same or different routes of administration. The compound(s) of formula (I) and the anticonvulsant(s) or contraceptive agent(s) may be administered via the same or different routes of administration.

Suitable examples of methods of administration are orally, intravenous (iv), intramuscular (im), and subcutaneous (sc). Compounds may also be administrated directly to the nervous system including, but not limited to the intracerebral, intraventricular, intracerebroventricular, intrathecal, intracisternal, intraspinal and/or peri-spinal routes of administration by delivery via intracranial or intravertebral needles and/or catheters with or without pump devices.

The compound(s) of formula (I) and the anticonvulsant(s) or contraceptive agent(s) may be administered according to simultaneous or alternating regimens, at the same or different times during the course of the therapy, concurrently in divided or single forms.

Optimal dosages to be administered may be readily determined by those skilled in the art, and will vary with the particular compound used, the mode of administration, and the strength of the preparation and the advancement of the disease condition. In addition, factors associated with the particular patient being treated, including patient's sex, age, weight, diet, time of administration and concomitant diseases, will result in the need to adjust dosages.

The term "CB receptor mediated syndrome, disorder, or disease" refers to syndromes, disorders or diseases associated with a biological response mediated by a CB receptor such that there is discomfort or decreased life expectancy to the organism.

CB receptor mediated syndromes, disorders or diseases can occur in both animals and humans and include appetite, metabolism, diabetes, obesity, glaucoma-associated intraocular pressure, social, mood, seizure, substance abuse, learning, cognition, memory, organ contraction, muscle spasm, bowel, respiratory, locomotor activity, movement, immune, inflammation, cell growth, pain or neurodegenerative related syndromes, disorders or diseases.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

Diabetes related syndromes, disorders or diseases include glucose dysregulation, insulin resistance, glucose intolerance, hyperinsulinemia, dyslipidemia, hypertension, obesity and the like.

Type II diabetes mellitus (non-insulin-dependent diabetes mellitus) is a metabolic disorder (i.e., a metabolism related syndrome, disorder or disease) in which glucose dysregulation and insulin resistance results in chronic, long-term medical complications for both adolescents and adults affecting the eyes, kidneys, nerves and blood vessels and can lead to blindness, end-stage renal disease, myocardial infarction or limb amputation and the like. Glucose dysregulation includes the inability to make sufficient insulin (abnormal insulin secretion) and the inability to effectively use insulin (resistance to insulin action in target organs and tissues). Individuals suffering from Type II diabetes mellitus have a relative insulin deficiency. That is, in such individuals, plasma insulin levels are normal to high in absolute terms, although they are lower than predicted for the level of plasma glucose that is present.

Type II diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension. These micro- and macro-vascular complications can lead to blindness, end-stage renal disease, limb amputation and myocardial infarction.

Insulin Resistance Syndrome (IRS) (also referred to as Syndrome X, Metabolic Syndrome or Metabolic Syndrome X) is a disorder that presents risk factors for the development of Type II diabetes and cardiovascular disease including glucose intolerance, hyperinsulinemia, insulin resistance, dyslipidemia (e.g. high triglycerides, low HDL-cholesterol and the like), hypertension and obesity.

Social or mood related syndromes, disorders or diseases include depression, anxiety, psychosis, social affective disorders or cognitive disorders and the like.

Substance abuse related syndromes, disorders or diseases include drug abuse, drug withdrawal, alcohol abuse, alcohol withdrawal, nicotine withdrawal, cocaine abuse, cocaine withdrawal, heroin abuse, heroin withdrawal and the like.

Learning, cognition or memory related syndromes, disorders or diseases include memory loss or impairment as a result of age, disease, side effects of medications (adverse events) and the like.

Muscle spasm syndromes, disorders or diseases include multiple sclerosis, cerebral palsy and the like.

Locomotor activity and movement syndromes, disorders or diseases include stroke, Parkinson's disease, multiple sclerosis, epilepsy and the like.

Bowel related syndromes, disorders or diseases include bowel dysmotility associated disorders (either accompanied by pain, diarrhea or constipation or without), irritable bowel syndrome (and other forms of bowel dysmotility and the like), inflammatory bowel diseases (such as ulcerative colitis, Crohn's disease and the like) and celiac disease.

Respiratory related syndromes, disorders or diseases include chronic pulmonary obstructive disorder, emphysema, asthma, bronchitis and the like.

Immune or inflammation related syndromes, disorders or diseases include allergy, rheumatoid arthritis, dermatitis, autoimmune disease, immunodeficiency, chronic neuropathic pain and the like.

Cell growth related syndromes, disorders or diseases include dysregulated mammalian cell proliferation, breast cancer cell proliferation, prostrate cancer cell proliferation and the like.

Pain related syndromes, disorders or diseases include central and peripheral pathway mediated pain, bone and joint pain, migraine headache associated pain, cancer pain, menstrual cramps, labor pain and the like.

Neurodegenerative related syndromes, disorders or diseases include Parkinson's Disease, multiple sclerosis, epilepsy, ischemia or secondary biochemical injury collateral to traumatic head or brain injury, brain inflammation, eye injury or stroke and the like.

The present invention includes a method for treating, ameliorating or preventing a cannabinoid receptor agonist mediated syndrome, disorder or disease in a subject in need thereof comprising the step of administering to the subject an effective amount of a cannabinoid agonist compound of the present invention or composition thereof.

The present invention includes a method for treating, ameliorating or preventing a cannabinoid receptor agonist mediated syndrome, disorder or disease in a subject in need thereof comprising the step of administering to the subject an effective amount of a cannabinoid agonist compound of the present invention in a combination product and/or therapy with an anticonvulsant or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention in a combination product and/or therapy with an anticonvulsant or composition thereof.

The present invention includes a method for treating, ameliorating or preventing a cannabinoid receptor inverse-agonist mediated syndrome, disorder or disease in a subject in need thereof comprising the step of administering to the subject an effective amount of a cannabinoid inverse-agonist compound of the present invention in a combination product and/or therapy with one or more contraceptives or composition thereof.

The present invention includes a method for treating, ameliorating or preventing a cannabinoid receptor antagonist mediated syndrome, disorder or disease in a subject in need thereof comprising the step of administering to the subject an effective amount of a cannabinoid antagonist compound of the present invention or composition thereof.

The present invention includes a method for treating, ameliorating or preventing a cannabinoid receptor antagonist mediated syndrome, disorder or disease in a subject in need thereof comprising the step of administering to the subject an effective amount of a cannabinoid antagonist compound of the present invention in a combination product and/or therapy with an anticonvulsant or composition thereof.

The present invention includes a method for treating, ameliorating or preventing a cannabinoid receptor antagonist mediated syndrome, disorder or disease in a subject in need thereof comprising the step of administering to the subject a therapeutically or prophylactically effective amount of a cannabinoid antagonist compound of the present invention in a combination product and/or therapy with one or more contraceptives or composition thereof.

The present invention includes a method for treating, ameliorating or preventing a CB1 receptor agonist mediated syndrome, disorder or disease in a subject in need thereof comprising the step of administering to the subject an effective amount of a CB1 agonist compound of the present invention or composition thereof.

The present invention includes a method for treating, ameliorating or preventing a CB1 receptor agonist mediated syndrome, disorder or disease in a subject in need thereof comprising the step of administering to the subject an effective amount of a CB1 agonist compound of the present invention in a combination product and/or therapy with an anticonvulsant or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention in a combination product and/or therapy with an anticonvulsant or composition thereof.

The present invention includes a method for treating, ameliorating or preventing a CB1 receptor inverse-agonist mediated syndrome, disorder or disease in a subject in need thereof comprising the step of administering to the subject an effective amount of a CB1 inverse-agonist compound of the present invention in a combination product and/or therapy with one or more contraceptives or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention in a combination product and/or therapy with an anticonvulsant or composition thereof.

The present invention includes a method for treating, ameliorating or preventing a CB1 receptor inverse-agonist mediated appetite related obesity related or metabolism related syndrome, disorder or disease in a subject in need thereof comprising the step of administering to the subject an effective amount of a CB1 inverse-agonist compound of the present invention in a combination product and/or therapy with one or more contraceptives or composition thereof.

Appetite related syndromes, disorders or diseases include obesity, overweight condition, anorexia, bulimia, cachexia, dysregulated appetite and the like.

Obesity related syndromes, disorders or diseases include obesity as a result of genetics, diet, food intake volume, metabolic syndrome, disorder or disease, hypothalmic disorder or disease, age, reduced activity, abnormal adipose mass distribution, abnormal adipose compartment distribution and the like.

Metabolism related syndromes, disorders or diseases include metabolic syndrome, dyslipidemia, elevated blood pressure, diabetes, insulin sensitivity or resistance, hyperinsulinemia, hypercholesterolemia, hyperlipidemias, hypertriglyceridemias, atherosclerosis, hepatomegaly, steatosis, abnormal alanine aminotransferase levels, inflammation, atherosclerosis and the like.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention or composition thereof.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention in a combination product and/or therapy with an anticonvulsant or composition thereof.

The present invention includes a method for treating, ameliorating or preventing a CB1 receptor antagonist mediated syndrome, disorder or disease in a subject in need thereof comprising the step of administering to the subject an effective amount of a CB1 antagonist compound of the present invention in a combination product and/or therapy with one or more contraceptives or composition thereof.

The present invention includes a method for treating, ameliorating or preventing a CB2 receptor agonist mediated syndrome, disorder or disease in a subject in need thereof comprising the step of administering to the subject an effective amount of a CB2 agonist compound of the present invention or composition thereof.

The present invention includes a method for treating, ameliorating or preventing a CB2 receptor agonist mediated syndrome, disorder or disease in a subject in need thereof comprising the step of administering to the subject an effective amount of a CB2 agonist compound of the present invention in a combination product and/or therapy with an anticonvulsant or composition thereof.

The present invention includes include a method for treating, ameliorating or preventing a CB2 receptor inverse-agonist mediated syndrome, disorder or disease in a subject in need thereof comprising the step of administering to the subject an effective amount of a CB2 inverse-agonist compound of the present invention or composition thereof.

The present invention includes a method for treating, ameliorating or preventing a CB2 receptor inverse-agonist mediated syndrome, disorder or disease in a subject in need thereof comprising the step of administering to the subject an effective amount of a CB2 inverse-agonist compound of the present invention in a combination product and/or therapy with an anticonvulsant or composition thereof.

The present invention includes a method for treating, ameliorating or preventing a CB2 receptor antagonist mediated syndrome, disorder or disease in a subject in need thereof comprising the step of administering to the subject an effective amount of a CB2 antagonist compound of the present invention or composition thereof.

The present invention includes a method for treating, ameliorating or preventing a CB2 receptor antagonist mediated syndrome, disorder or disease in a subject in need thereof comprising the step of administering to the subject an effective amount of a CB2 antagonist compound of the present invention in a combination product and/or therapy with an anticonvulsant or composition thereof.

The present invention includes a method for treating, ameliorating or preventing a metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising the step of administering to the subject an effective amount of a compound of the present invention or composition thereof.

The present invention includes a method for treating, ameliorating or preventing a metabolism related syndrome, disorder or disease, an appetite related syndrome, disorder or disease, a diabetes related syndrome, disorder or disease, an obesity related syndrome, disorder or disease or a learning, cognition or memory related syndrome, disorder or disease in a subject in need thereof comprising the step of administering to the subject an effective amount of a compound of the present invention in a combination product and/or therapy with an anticonvulsant or composition thereof.

The present invention includes a pharmaceutical composition or medicament comprising an admixture of a compound of the present invention and an optional pharmaceutically acceptable carrier.

The present invention includes a pharmaceutical composition or medicament comprising an admixture of two or more compounds of the present invention and an optional pharmaceutically acceptable carrier.

The present invention also includes a pharmaceutical composition or medicament comprising an admixture of a compound of formula (I), an anticonvulsant and an optional pharmaceutically acceptable carrier.

Such pharmaceutical compositions are particularly useful for treating a subject suffering from a metabolism related syndrome, disorder or disease, an appetite related syndrome, disorder or disease, a diabetes related syndrome, disorder or disease, an obesity related syndrome, disorder or disease, or a learning, cognition or memory related syndrome, disorder or disease.

Anticonvulsants useful in the methods and compositions of the present invention in combination with a compound of formula (I) or (Ia) include, but are not limited to, topiramate, analogs of topiramate, carbamazepine, valproic acid, lamotrigine, gabapentin, phenyloin and the like and mixtures or pharmaceutically acceptable salts thereof.

Topiramate, 2,3:4,5-bis-O-(1-methylethylidene)-β-D-fructopyranose sulfamate, is currently marketed for the treatment of seizures in patients with simple and complex partial epilepsy and seizures in patients with primary or secondary generalized seizures in the United States, Europe and most other markets throughout the world. Topiramate is currently available for oral administration in round tablets containing 25 mg, 100 mg or 200 mg of active agent, and as 15 mg and 25 mg sprinkle capsules for oral administration as whole capsules or opened and sprinkled onto soft food. U.S. Pat. No. 4,513,006, incorporated herein by reference, discloses topiramate and analogs of topiramate, their manufacture and use for treating epilepsy. Additionally, topiramate may also be made by the process disclosed in U.S. Pat. Nos. 5,242,942 and 5,384,327, which are incorporated by reference herein. The term "analogs of topiramate", as used herein, refers to the sulfamate compounds of formula (I), which are disclosed in U.S. Pat. No. 4,513,006 (see, e.g., column 1, lines 36-65 of U.S. Pat. No. 4,513,006).

For use in the methods of the present invention in combination with a compound of the formula (I) or (Ia), topiramate (or an analog of topiramate) can be administered in the range of about 10 to about 1000 mg daily, preferably in the range of about 10 to about 650 mg daily, more preferably in the range of about 15 to about 325 mg once or twice daily.

Carbamazepine, 5H-dibenz[b,f]azepine-5-carboxamide, is an anticonvulsant and specific analgesic for trigeminal neuralgia, available for oral administration as chewable tablets of 100 mg, tablets of 200 mg, XR (extended release) tablets of 100, 200, and 400 mg, and as a suspension of 100 mg/5 mL (teaspoon); U.S. Pat. No. 2,948,718, herein incorporated by reference in its entirety, discloses carbamazepine and its methods of use.

For use in the methods of the present invention in combination with a compound of the formula (I) or (Ia), carbamazepine can be administered in the range of about 200 to about 1200 mg/day; preferably, about 400 mg/day.

Valproic acid, 2-propylpentanoic acid or dipropylacetic acid, is an antiepileptic agent commercially available as soft elastic capsules containing 250 mg valproic acid, and as syrup containing the equivalent of 250 mg valproic acid per 5 mL as the sodium salt. Valproic acid and various pharmaceutically acceptable salts are disclosed in U.S. Pat. No. 4,699,927, which is incorporated by reference herein in its entirety.

For use in the methods of the present invention in combination with a compound of the formula (I) or (Ia), valproic acid can be administered in the range of about 250 to about 2500 mg/day; preferably, about 1000 mg/day.

Lamotrigine, 3,5-diamino-6-(2,3-dichlorophenyl)-1,2,4-triazine, is an antiepileptic drug commercially available for oral administration as tablets containing 25 mg, 100 mg, 150 mg, and 200 mg of lamotrigine, and as chewable dispersible tablets containing 2 mg, 5 mg, or 25 mg of lamotrigine. Lamotrigine and its uses are disclosed in U.S. Pat. No. 4,486,354, incorporated by reference herein in its entirety.

For use in the methods of the present invention in combination with a compound of the formula (I) or (Ia), lamotrigine can be administered in the range of about 50 to about 600 mg/day in one to two doses; preferably, about 200 to about 400 mg/day; most preferably, about 200 mg/day.

Gabapentin, 1-(aminomethyl)cyclohexaneacetic acid, is commercially available for the adjunctive treatment of epilepsy and for postherpetic neuralgia in adults as capsules containing 100 mg, 300 mg, and 400 mg of gabapentin, film-coated tablets containing 600 mg and 800 mg of gabapentin, and an oral solution containing 250 mg/5 mL of gabapentin. Gabapentin and its methods of use are described in U.S. Pat. Nos. 4,024,175 and 4,087,544, herein incorporated by reference in their entirety.

For use in the methods of the present invention in combination with a compound of the formula (I) or (Ia), gabapentin can be administered in the range of about 300 to about 3600 mg/day in two to three divided doses; preferably, about 300 to about 1800 mg/day; most preferably, about 900 mg/day.

Phenyloin sodium, 5,5-diphenylhydantoin sodium salt, is an anticonvulsant, which is commercially available for oral administration as capsules containing 100 mg, 200 mg or 300 mg of phenyloin sodium.

For use in the methods of the present invention in combination with a compound of the formula (I) or (Ia), phenyloin sodium can be administered in the range of about 100 to about 500 mg/day; preferably, about 300 to about 400 mg/day; most preferably, about 300 mg/day.

The present invention also includes a pharmaceutical composition or medicament comprising an admixture of a compound of formula (I) or (Ia), one or more contraceptives and an optional pharmaceutically acceptable carrier.

Contraceptives suitable for use in a combination product and/or therapy include, for example, ORTHO CYCLEN®, ORTHO TRI-CYCLEN®, ORTHO TRI-CYCLEN LO®, and ORTHO EVRA®, all available from Ortho-McNeil Pharmaceutical, Inc., Raritan, N.J. It should also be understood that contraceptives suitable for use in the invention encompass those contraceptives that include a folic acid component.

Smoking and/or obesity have been identified as risk factors in women taking oral contraceptives. CB1 receptor antagonists and inverse agonists have been found to be useful therapeutic agents for reducing the urge to smoke and for assisting patients with eating disorders to lose weight.

Accordingly, the invention further includes a method of reducing the risk factors associated with smoking and/or obesity for women taking contraceptives by co-administering with a contraceptive at least one of a CB1 receptor antagonist and/or CB1 receptor inverse-agonist compound of formula (I) or (Ia).

The use of such compounds or a pharmaceutical composition or medicament thereof is to reduce the desire to smoke and/or to assist in weight loss for patients taking contraceptives.

Pharmaceutical Compositions

The term "composition" refers to a product comprising the specified ingredients in the specified amounts, as well as any product that results, directly or indirectly, from combinations of the specified ingredients in the specified amounts. The invention further comprises mixing one or more of the compounds of the invention and a pharmaceutically acceptable carrier; and, includes those compositions resulting from such a process. Contemplated processes include both traditional and modern pharmaceutical techniques.

Pharmaceutical compositions of the invention may, alternatively or in addition to a compound of formula (I) or (Ia), comprise a pharmaceutically acceptable salt of a compound of formula (I) or (Ia) or a prodrug or pharmaceutically active metabolite of such a compound or salt in admixture with a pharmaceutically acceptable carrier.

The term "medicament" refers to a product for use in treating, ameliorating or preventing a cannabinoid receptor mediated syndrome, disorder or disease.

"Pharmaceutically acceptable carrier" means molecular entities and compositions that are of sufficient purity and quality for use in the formulation of a composition of the invention and that, when appropriately administered to an animal or a human, do not produce an adverse, allergic, or other untoward reaction.

Since both clinical and veterinary uses are equally included within the scope of the present invention, a pharmaceutically acceptable formulation would include a composition or medicament formulation for either clinical or veterinary use.

The present invention includes a process for making the composition or medicament comprising mixing any of the instant compounds and a pharmaceutically acceptable carrier and include those compositions or medicaments resulting from such a process. Contemplated processes include both conventional and unconventional pharmaceutical techniques. Other examples include a composition or medicament comprising a mixture of at least two of the instant compounds in association with a pharmaceutically acceptable carrier.

The composition or medicament may be administered in a wide variety of dosage unit forms depending on the method of administration; wherein such methods include (without limitation) oral, sublingual, nasal (inhaled or insufflated), transdermal, rectal, vaginal, topical (with or without occlusion), intravenous (bolus or infusion) or for injection (intraperitoneally, subcutaneously, intramuscularly, intratumorally or parenterally) using a suitable dosage form well known to those of ordinary skill in the area of pharmaceutical administration. Accordingly, the term "dosage unit" or "dosage form" is alternatively used to refer to (without limitation) a tablet, pill, capsule, solution, syrup, elixir, emulsion, suspension, suppository, powder, granule or sterile solution, emulsion or suspension (for injection from an ampoule or using a device such as an auto-injector or for use as an aerosol, spray or drop). Furthermore, the composition may be provided in a form suitable for weekly or monthly administration (e.g. as an insoluble salt of the active compound (such as the decanoate salt) adapted to provide a depot preparation for intramuscular injection).

In preparing a dosage form, the principal active ingredient (such as a compound of the present invention or a pharmaceutically acceptable salt, racemate, enantiomer, or diastereomer thereof) is optionally mixed with one or more pharmaceutical carriers (such as a starch, sugar, diluent, granulating agent, lubricant, glidant, binder, disintegrating agent and the like), one or more inert pharmaceutical excipients (such as water, glycols, oils, alcohols, flavoring agents, preservatives, coloring agents, syrup and the like), one or more conventional tableting ingredient (such as corn starch, lactose, sucrose, sorbitol, talc, stearic acid, magnesium stearate, dicalcium phosphate, any of a variety of gums and the like) and a diluent (such as water and the like) to form a homogeneous composition (whereby the active ingredient is dispersed or suspended evenly throughout the mixture) which may be readily subdivided into dosage units containing equal amounts of a compound of the present invention.

Binders include, without limitation, starch, gelatin, natural sugars (such as glucose, beta-lactose and the like), corn sweeteners and natural and synthetic gums (such as acacia, tragacanth, sodium oleate, sodium stearate, magnesium stearate, sodium benzoate, sodium acetate, sodium chloride and the like). Disintegrating agents include, without limitation, starch, methyl cellulose, agar, bentonite, xanthan gum and the like.

Because of the ease of administration, tablets and capsules represent an advantageous oral dosage unit form, wherein solid pharmaceutical carriers are employed. If desired, tablets may be sugar or film coated or enteric-coated by standard techniques. Tablets may also be coated or otherwise compounded to provide a prolonged therapeutic effect. For example, the dosage form may comprise an inner dosage and an outer dosage component, whereby the outer component is in the form of an envelope over the inner component. The two components may further be separated by a layer, which resists disintegration in the stomach (such as an enteric layer) and permits the inner component to pass intact into the duodenum or a layer which delays or sustains release. A variety of enteric and nonenteric layer or coating materials may be used (such as polymeric acids, shellacs, acetyl alcohol, cellulose acetate and the like) or combinations thereof.

The liquid forms in which a compound of the present invention may be incorporated for oral administration include (without limitation), aqueous solutions, suitably flavored syrups, aqueous or oil suspensions (using a suitable synthetic or natural gum dispersing or suspending agent such as tragacanth, acacia, alginate, dextran, sodium carboxymethylcellulose, methylcellulose, polyvinyl-pyrrolidone, gelatin and the like), flavored emulsions (using a suitable edible oil such as cottonseed oil, sesame oil, coconut oil, peanut oil and the like), elixirs and other similar liquid forms with a variety of pharmaceutically acceptable vehicles.

As is also known in the art, the compounds may alternatively be administered parenterally via injection. For parenteral administration, sterile solutions or injectable suspensions may be parenteral vehicles wherein appropriate liquid carriers, suspending agents and the like are employed. Sterile solutions are a preferred parenteral vehicle. Isotonic preparations that generally contain suitable preservatives are employed when intravenous administration is desired. A parenteral formulation may consist of the active ingredient dissolved in or mixed with an appropriate inert liquid carrier. Acceptable liquid carriers comprise aqueous solvents and the like and other optional ingredients for aiding solubility or preservation. Such aqueous solvents include sterile water, Ringer's solution or an isotonic aqueous saline solution. Alternatively, a sterile non-volatile oil may be employed as a solvent agent. Other optional ingredients include vegetable oils (such as peanut oil, cottonseed oil, sesame oil and the like), organic solvents (such as solketal, glycerol, formyl and the like), preservatives, isotonizers, solubilizers, stabilizers, pain-soothing agents and the like. A parenteral formulation is prepared by dissolving or suspending the active ingredient in the liquid carrier whereby the final dosage unit contains from 0.005 to 10% by weight of the active ingredient.

Compounds of the present invention may be administered intranasally using a suitable intranasal vehicle. Compounds of the present invention may be administered topically using a suitable topical transdermal vehicle or a transdermal patch. Administration via a transdermal delivery system requires a continuous rather than intermittent dosage regimen.

Compounds of the present invention may also be administered via a rapid dissolving or a slow release composition, wherein the composition includes a biodegradable rapid dissolving or slow release carrier (such as a polymer carrier and the like) and a compound of the invention. Rapid dissolving or slow release carriers are well known in the art and are used to form complexes that capture therein an active compound(s) and either rapidly or slowly degrade/dissolve in a suitable environment (e.g., aqueous, acidic, basic, etc). Such particles are useful because they degrade/dissolve in body fluids and release the active compound(s) therein. The particle size of a compound of the present invention, carrier or any excipient used in such a composition may be optimally adjusted using techniques known to those of ordinary skill in the art.

The present invention includes a composition of an instant compound or prodrug thereof present in a prophylactically or therapeutically effective amount necessary for symptomatic relief to a subject in need thereof A prophylactically or therapeutically effective amount of an instant compound or prodrug thereof may range from about 0.01 ng to about 1 g and may be constituted into any form suitable for the administration method and regimen selected for the subject.

Depending on the subject and disease to be treated, the prophylactically or therapeutically effective amount for a person of average body weight of about 70 kg per day may range from about 0.01 ng/kg to about 300 mg/kg; from about 0.1 ng/kg to about 200 mg/kg; from about 0.5 ng/kg to about 100 mg/kg; or, from about 0.1 ng/kg to about 50 mg/kg.

An optimal prophylactically or therapeutically effective amount and administration method and regimen may be readily determined by those skilled in the art, and will vary depending on factors associated with the particular patient being treated (age, weight, diet and time of administration), the severity of the condition being treated, the compound and dosage unit being employed, the mode of administration and the strength of the preparation.

Dosage unit(s) may be administered to achieve the therapeutically or prophylactically effective amount in a regimen of from about once per day to about 5 times per day. The preferred dosage unit for oral administration is a tablet containing 0.01, 0.05, 0.1, 0.5, 1.0, 2.5, 5.0, 10.0, 15.0, 25.0, 50.0, 100, 150, 200, 250 or 500 mg of the active ingredient.

Representative compounds for use in the therapeutic methods and pharmaceutical compositions described herein include compounds selected from:

| Cpd | Name |
| --- | --- |
| 1 | 1-cyclohexyl-4,5,6,7,8,9-hexahydro-1H-cyclooctapyrazole-3-carboxylic acid (1,3,3-trimethyl-bicyclo[2.2.1]hept-2-yl)-amide, |
| 2 | 1-cyclohexyl-4,5,6,7,8,9-hexahydro-1H-cyclooctapyrazole-3-carboxylic acid (adamantan-1-ylmethyl)-amide, |
| 3 | 1-cyclopentyl-4,5,6,7,8,9-hexahydro-1H-cyclooctapyrazole-3-carboxylic acid (adamantan-1-ylmethyl)-amide, |
| 4 | 2-[(1-cyclohexyl-4,5,6,7,8,9-hexahydro-1H-cyclooctapyrazole-3-carbonyl)-amino]-bicyclo[2.2.1]heptane-2-carboxylic acid ethyl ester, |
| 5 | 1-cyclopentyl-4,5,6,7,8,9-hexahydro-1H-cyclooctapyrazole-3-carboxylic acid (1-adamantan-1-yl-ethyl)-amide, |
| 6 | 1-cyclohexyl-4,5,6,7,8,9-hexahydro-1H-cyclooctapyrazole-3-carboxylic acid (1-adamantan-1-yl-ethyl)-amide, |
| 11 | (9E)-1-(2,4-dichloro-phenyl)-9-(4-fluoro-benzylidene)-4,5,6,7,8,9-hexahydro-1H-cyclooctapyrazole-3-carboxylic acid N'-(2,4-dichloro-phenyl)-hydrazide, |
| 12 | (9E)-1-(2,4-dichloro-phenyl)-9-(4-fluoro-benzylidene)-4,5,6,7,8,9-hexahydro-1H-cyclooctapyrazole-3-carboxylic acid [(1R)-1-phenyl-ethyl]-amide, |
| 13 | (9E)-1-(2,4-dichloro-phenyl)-9-(4-fluoro-benzylidene)-4,5,6,7,8,9-hexahydro-1H-cyclooctapyrazole-3-carboxylic acid [(1R)-1-pyridin-2-yl-ethyl]-amide, |
| 14 | (9E)-[1-(2,4-dichloro-phenyl)-9-(4-fluoro-benzylidene)-4,5,6,7,8,9-hexahydro-1H-cyclooctapyrazol-3-yl]-piperidin-1-yl-methanone, |
| 15 | (9E)-1-(2,4-dichloro-phenyl)-9-(4-fluoro-benzylidene)-4,5,6,7,8,9-hexahydro-1H-cyclooctapyrazole-3-carboxylic acid [(1S)-1-phenyl-ethyl]-amide, |
| 16 | (9E)-1-(2,4-dichloro-phenyl)-9-(4-fluoro-benzylidene)-4,5,6,7,8,9-hexahydro-1H-cyclooctapyrazole-3-carboxylic acid [(1S)-1-cyclohexyl-ethyl]-amide, |
| 17 | (9E)-1-(2,4-dichloro-phenyl)-9-(4-fluoro-benzylidene)-4,5,6,7,8,9-hexahydro-1H-cyclooctapyrazole-3-carboxylic acid [(1R)-1-cyclohexyl-ethyl]-amide, |
| 18 | (9E)-1-(2,4-dichloro-phenyl)-9-(4-fluoro-benzylidene)-4,5,6,7,8,9-hexahydro-1H-cyclooctapyrazole-3-carboxylic acid (hexahydro-cyclopenta[c]pyrrol-2-yl)-amide, or |
| 19 | (9E)-1-(2,4-dichloro-phenyl)-9-(4-fluoro-benzylidene)-4,5,6,7,8,9-hexahydro-1H-cyclooctapyrazole-3-carboxylic acid piperidin-1-ylamide. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations and formulae have the indicated meanings:

| Abbreviation | Meaning |
|---|---|
| Cpd | compound |
| EDCI | 1-(3-dimethylaminopropyl)-3-ethylcarbodiimide |
| DCM | dichloromethane |
| DMAP | 4-dimethylaminopyridine |
| EtOAc | ethyl acetate |
| Et$_2$O | anhydrous ether |
| K$_2$CO$_3$ | potassium carbonate |
| LDA | lithium diisopropylamine |
| LHMDS or LiHMDS | lithium bis(trimethylsilyl)amide |
| min(s)/hr(s) | minute(s)/hour(s) |
| N$_2$ | nitrogen |
| RT/rt/r.t. | room temperature |
| SOCl$_2$ | thionyl chloride |
| TEA or Et$_3$N | triethylamine |
| THF | tetrahydrofuran |

Scheme A

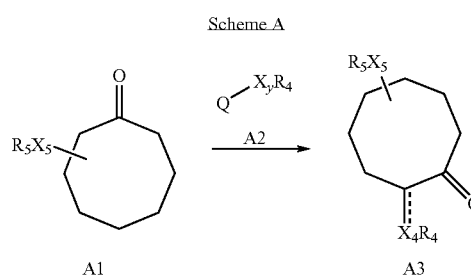

A solution of cyclooctanone Compound A1 (in a solvent such as THF and the like) is reacted with a Compound A2 (in a solvent such as anhydrous THF and the like, wherein Q-X$_y$ represents a suitable reaction group and wherein certain portions of Q-X$_y$ are incorporated into X$_4$R$_4$ as a product of the reaction) under basic conditions to provide Compound A3.

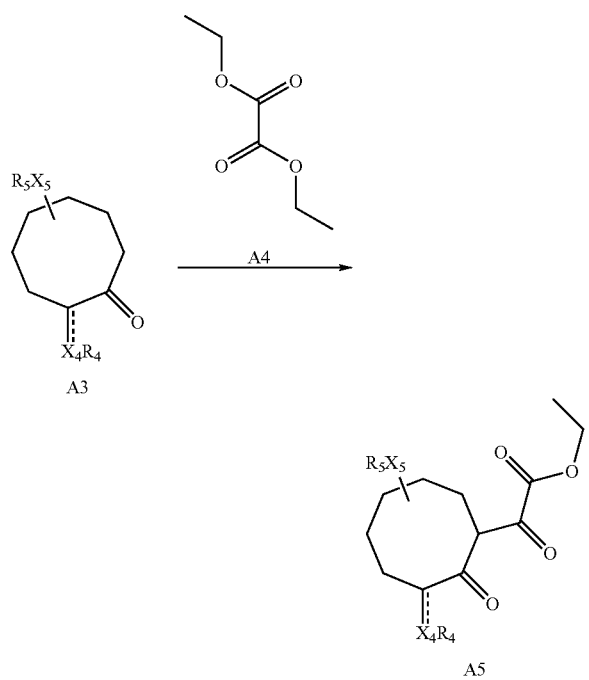

A solution of Compound A3 (in a solvent such as Et$_2$O, THF and the like or a mixture thereof) is added dropwise to a reagent solution (such as LHMDS and the like in a solvent such as Et$_2$O or THF and the like or a mixture thereof) at −78° C. under an inert atmosphere and stirred at about −78° C. for about 40 mins. A solution of Compound A4 (in a solvent such as Et$_2$O and the like) is added dropwise and the mixture is stirred at about −78° C. for about 1 hr, then allowed to warm to r.t. over a period of about 2 hrs to yield Compound A5 as a crude product used without further purification in the next step.

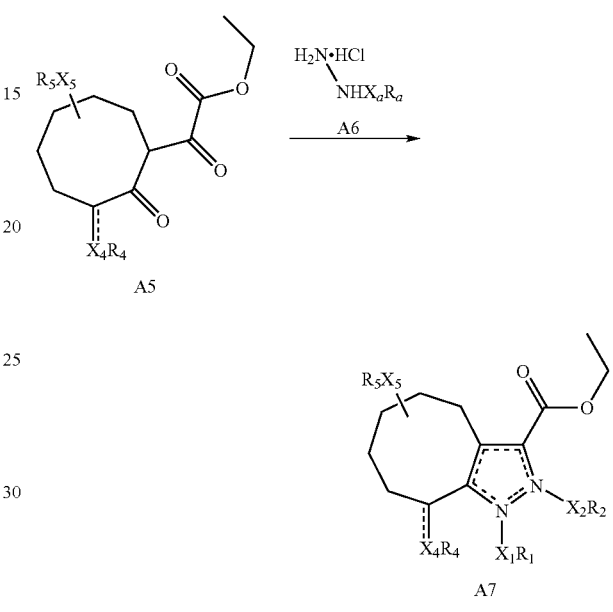

A reagent (such as K$_2$CO$_3$ and the like) and a substituted hydrazine mono or dihydrochloride Compound A6 are added to a solution of Compound A5 (in a solvent such as one or more of MeOH, EtOH, CH$_2$Cl$_2$ and the like) at a temperature of about 0° C. under an inert atmosphere. The mixture was stirred overnight, while warming to r.t., to provide Compound A7 after workup.

The X$_a$R$_a$ substituent moiety on Compound A6 represents the possibility that, after isomer separation, the substituted amine group may be found either on the N$^1$ position as X$_1$R$_1$ or on the N$^2$ position as X$_2$R$_2$. Compound A7 represents a mixture of isomers, wherein a mixture of X$_1$R$_1$ and X$_2$R$_2$ isomers are present.

The hydrazine hydrochloride or dihydrochloride Compound A6 may be converted to the free base by methods known to those skilled in the art. In the examples of the present invention, the free base is prepared either in situ (as shown for illustrative purposes in this Scheme) or separately (then added to the reaction mixture) by reaction with K$_2$CO$_3$.

As illustrated in this Scheme, Compound A6 may also be further substituted with a variety of X$_a$R$_a$ substituents (as previously defined herein). In many instances, the substituted hydrazine Compound A6 is commercially available. When not commercially available, a particularly substituted Compound A6 may be prepared by methods known to those skilled in the art.

More specifically, a halogenated X$_a$R$_a$ substituent moiety is reacted with a hydrazine hydrate solution at reflux and used without further purification in place of Compound A6.

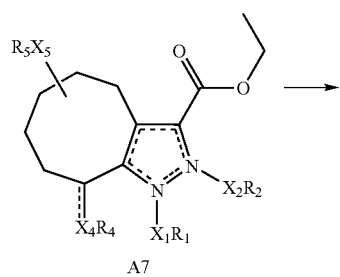

A7

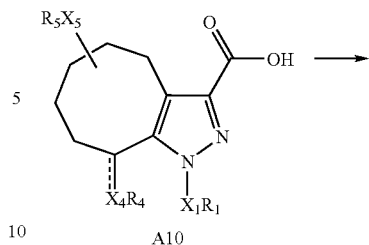

A10

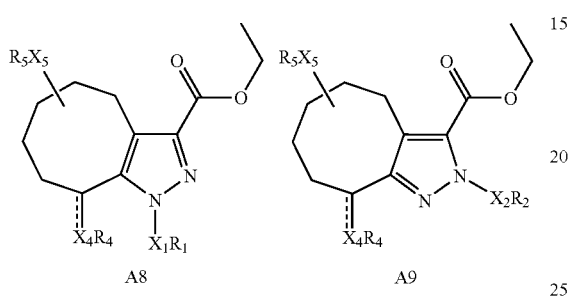

A8                                A9

The Compound A7 isomeric mixture is separated via flash chromatography (eluted with a suitable solvent mixture such as from about 20% to about 30% EtOAc and the like in hexane and the like) to provide a purified major isomer Compound A8 and a minor isomer Compound A9.

The major isomer Compound A8 is substituted on the $N^1$ position with $X_1R_1$ ($X_2R_2$ is necessarily absent). The minor isomer Compound A9 is substituted on the $N^2$ position with $X_2R_2$ (wherein $X_1R_1$ is absent).

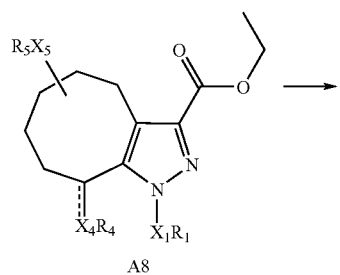

A8

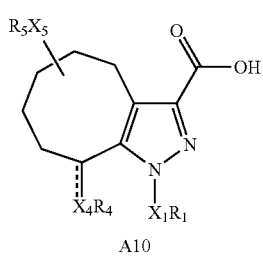

A10

The separated major isomer Compound A8 is treated with a reagent solution (such as a mixture of NaOH or LiOH in a solvent such as water, MeOH, THF and the like or a mixture thereof) and stirred overnight to provide Compound A10 after workup.

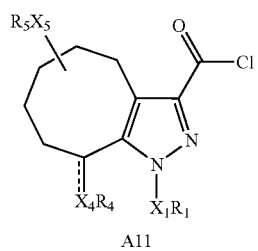

A11

A reagent solution (such as $SOCl_2$ and the like in a solvent such as $CH_2Cl_2$ and the like) is added to Compound A10 at ambient temperature under an inert nitrogen atmosphere. The reaction mixture is stirred at reflux temperature for about 15 mins to provide Compound A10 after workup.

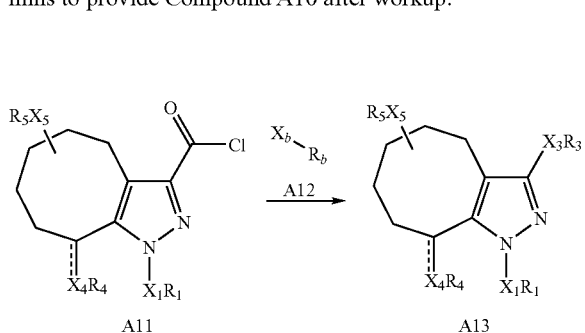

A11                                A13

A solution of Compound A10 (optionally mixed with TEA and the like) is added to a solution of a substituted amine Compound A12 (in a solvent such as $CH_2Cl_2$ and the like) at ambient temperature under an inert nitrogen atmosphere. The mixture is stirred at r.t. for a period of time to provide Compound A13 after workup.

For purposes of this Scheme, the $X_b$ portion of Compound A12 is an optionally substituted amino moiety, whereby the Compound A13 $X_3R_3$ substituent moiety incorporates the C(O) portion of the $C^3$ substituent of Compound A11 and the $X_b$ portion from $X_bR_b$ of Compound A12.

In general, Compound A12 is a commercially available substituted amine When not commercially available, a particularly substituted Compound A12 may be prepared by methods known to those skilled in the art amenable for reaction with a suitably prepared Compound A11.

For example, functional group transformations known to those skilled in the art may be used to prepare Compound A10 for reaction with a particularly substituted Compound A12 wherein $X_bR_b$ is an alkylsulfonylamino moiety or an alkylcarbamoyl moiety each further substituted on the amino portion.

The synthetic examples that follow herein describe more completely the preparation of particular compounds included within the scope of the present invention.

Example 1

1-cyclohexyl-4,5,6,7,8,9-hexahydro-1H-cyclooctapyrazole-3-carboxylic acid (1,3,3-trimethyl-bicyclo[2.2.1]hept-2-yl)-amide (Cpd 1)

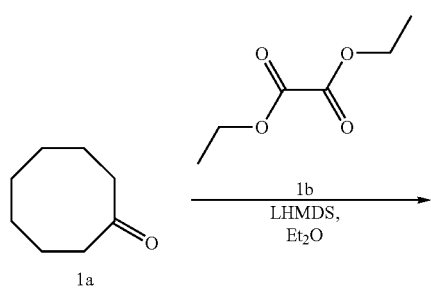

A solution of cyclooctanone Compound 1a (25.0 g, 0.20 Mol) in Et$_2$O (100 mL) was added dropwise to a solution of LHMDS (0.33 L, 0.20 Mol) in anhydrous Et$_2$O (200 mL) at −78° C. under a N$_2$ atmosphere. The mixture was maintained at −78° C. and stirred for 60 min. Compound 1b (29.2 g, 0.20 Mol) in anhydrous Et$_2$O (100 mL) was added dropwise and the mixture was stirred at −78° C. for 1 hr, then allowed to warm to r.t. over 3 hrs and stirred for 1 hr. The reaction mixture was quenched with water (100 mL) and diluted with EtOAc (300 mL), then the separated organic layer was washed with brine, dried with anhydrous sodium sulfate, then filtered and concentrated in vacuo. The resulting crude product was purified by flash chromatography (eluted with 20% EtOAc in hexane) to provide Compound 1c (36 g, 80%).

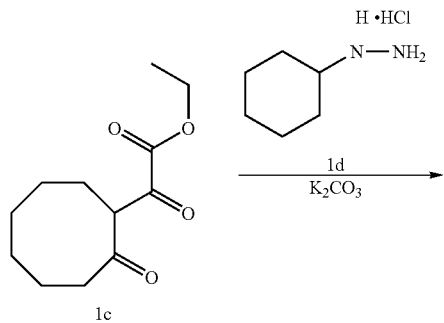

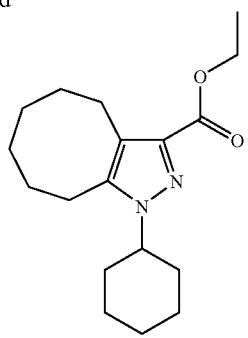

Cyclohexyl-hydrazine hydrochloride Compound 1d (2.5 g, 16.7 mMol) and K$_2$CO$_3$ (2.31 g, 16.7 mMol) were added to a solution of Compound 1c (3.7 g, 16.7 mMol) in EtOH (50 mL) at ambient temperature under a N$_2$ atmosphere. The reaction mixture was stirred overnight, then quenched with water (25 mL) and diluted with EtOAc (500 mL). The organic layer was separated, washed with brine and dried over anhydrous sodium sulfate, then filtered and concentrated in vacuo to provide Compound 1e (5 g), which was used in the next step without further purification.

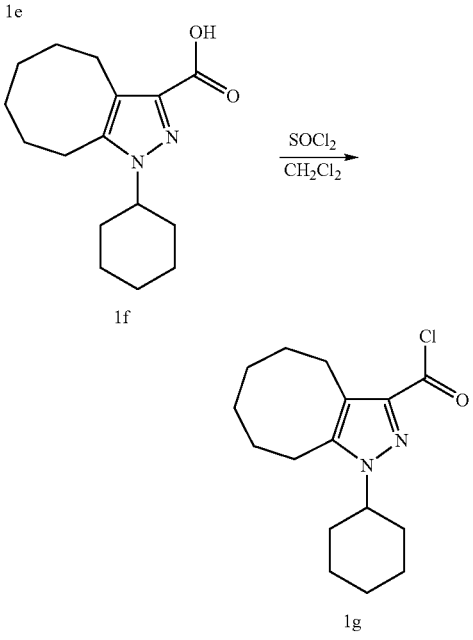

1N NaOH (50 mL) was added to Compound 1e (5 g, 16.4 mMol) in THF (25 mL). The mixture was stirred for 30 hours, acidified to pH 2 with 1N HCl and extracted with EtOAc (100 mL). The organic layer was washed with brine, dried over sodium sulfate, then filtered and concentrated in vacuo to yield Compound 1f as a white solid.

Thionyl chloride (5.87 g, 49.3 mMol) was added to a solution of Compound 1f in $CH_2Cl_2$ (50 mL) at ambient temperature under a $N_2$ atmosphere. The reaction was stirred for 3 hrs and concentrated in vacuo to provide Compound 1 g (4.5 g, 91%) as a light brown solid.

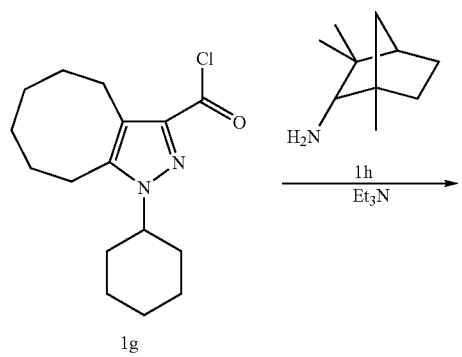

1g

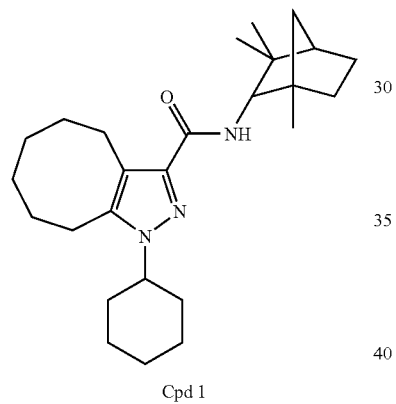

Cpd 1

A solution of Compound 1g (0.130 g, 0.46 mMol) in DCM (5 mL) was added dropwise to a solution of 1,3,3-trimethyl-bicyclo[2.2.1]hept-2-ylamine Compound 1h (0.87 g, 0.46 mMol) and $Et_3N$ (0.10 g, 0.98 mMol) in $CH_2Cl_2$ (10 mL) at ambient temperature under a $N_2$ atmosphere.

The reaction mixture was stirred at r.t. for 3 hrs, then diluted with water (10 mL) and $CH_2Cl_2$ (50 mL). The organic layer was separated and dried with anhydrous sodium sulfate, then filtered and concentrated in vacuo. The resulting crude oil was purified by flash chromatography using 20% EtOAc in hexane to provide Compound 1 (0.115 g, 63%) as a white solid. MS m/z 412 ($M^+$).

Following the procedure of Example 1, substituting the appropriate starting materials, reagents and solvents, the following compounds were prepared:

| Cpd | Name | MS |
|---|---|---|
| 2 | 1-cyclohexyl-4,5,6,7,8,9-hexahydro-1H-cyclooctapyrazole-3-carboxylic acid (adamantan-1-ylmethyl)-amide | 424 |
| 3 | 1-cyclopentyl-4,5,6,7,8,9-hexahydro-1H-cyclooctapyrazole-3-carboxylic acid (adamantan-1-ylmethyl)-amide | 410 |
| 4 | 2-[(1-cyclohexyl-4,5,6,7,8,9-hexahydro-1H-cyclooctapyrazole-3-carbonyl)-amino]-bicyclo[2.2.1]heptane-2-carboxylic acid ethyl ester | 442 |
| 5 | 1-cyclopentyl-4,5,6,7,8,9-hexahydro-1H-cyclooctapyrazole-3-carboxylic acid (1-adamantan-1-yl-ethyl)-amide | 424 |
| 6 | 1-cyclohexyl-4,5,6,7,8,9-hexahydro-1H-cyclooctapyrazole-3-carboxylic acid (1-adamantan-1-yl-ethyl)-amide | 438 |
| 7 | 1-cyclopentyl-4,5,6,7,8,9-hexahydro-1H-cyclooctapyrazole-3-carboxylic acid (1,3,3-trimethyl-bicyclo[2.2.1]hept-2-yl)-amide | 398 |
| 8 | 1-cyclobutyl-4,5,6,7,8,9-hexahydro-1H-cyclooctapyrazole-3-carboxylic acid (1,3,3-trimethyl-bicyclo[2.2.1]hept-2-yl)-amide | 384 |
| 9 | 1-cyclobutyl-4,5,6,7,8,9-hexahydro-1H-cyclooctapyrazole-3-carboxylic acid (adamantan-1-ylmethyl)-amide | 396 |
| 10 | 1-cyclobutyl-4,5,6,7,8,9-hexahydro-1H-cyclooctapyrazole-3-carboxylic acid (1-adamantan-1-yl-ethyl)-amide | 410 |

Example 2

(9E)-1-(2,4-dichloro-phenyl)-9-(4-fluoro-benzylidene)-4,5,6,7,8,9-hexahydro-1H-cyclooctapyrazole-3-carboxylic acid [(1S)-1-phenyl-ethyl]-amide (Cpd 15)

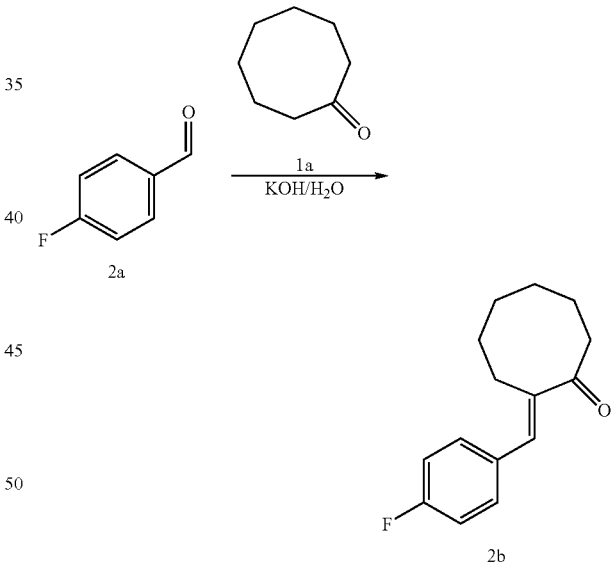

A solution of KOH (0.25 g, 4.46 mMol) in water (4.4 mL), was added to 4-fluoro-benzaldehyde Compound 2a (1.07 mL, 10 mMol) and the mixture was heated to 65° C. Cyclooctanone Compound 1a (1.26 g, 10 mMol) was added dropwise over a period of 15 mins. The mixture was refluxed for 5 hrs, then allowed to stir overnight at room temperature. The reaction mixture was acidified with 1N HCl (26 mL) and extracted with EtOAc (100 mL). The organic layer was washed with brine, dried over $Na_2SO_4$, then filtered and concentrated. The resulting yellow residue was purified on silica gel column with 3% EtOAc/Hexane to give (2E)-2-(4-fluoro-benzylidene)-cyclooctanone Compound 2b (1.04 g, 44.8%).

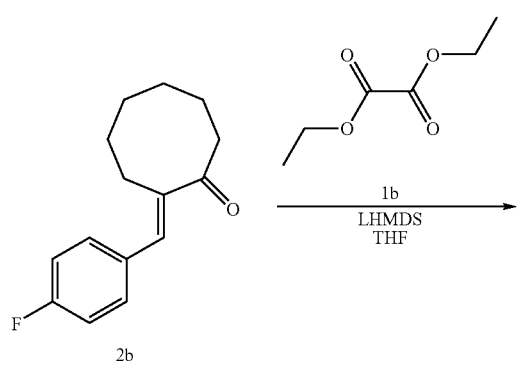

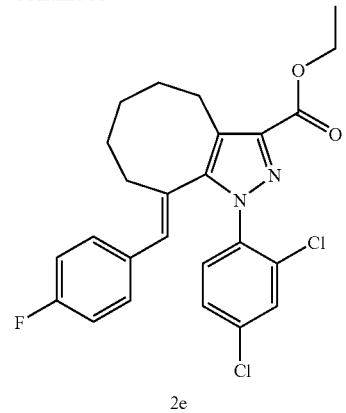

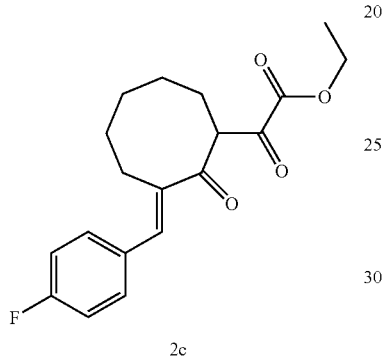

A solution of Compound 2b (1.04 g, 4.48 mMol) in THF (5 mL) was added dropwise to a solution of LHMDS (5.4 mL, 1M solution in THF) at −78° C. The resulting mixture was stirred at −78° C. for 1 hr, then oxalic acid diethyl ester Compound 1b (0.61 ml, 4.48 mmol) was added dropwise. The mixture was stirred at −78° C. for 1 hr, then allowed to gradually warm up to room temperature and stirred overnight at room temperature. The reaction mixture was acidified with 1N HCl and extracted with EtOAc (150 mL). The organic layer was washed with 1N HCl (1×) and water (2×) and dried over $Na_2SO_4$, then filtered and concentrated to give (3E)-[3-(4-fluoro-benzylidene)-2-oxo-cyclooctyl]-oxo-acetic acid ethyl ester Compound 2c as a yellow oil, which was used in the next step without further purification.

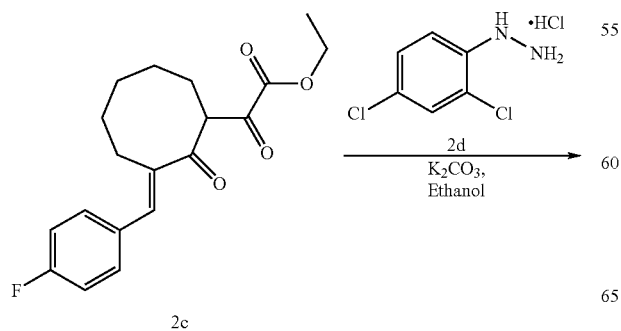

$K_2CO_3$ (0.62 g, 4.48 mmol) and (2,4-dichloro-phenyl)-hydrazine hydrochloride Compound 2d (0.96 g, 4.50 mmol) were added to a solution of Compound 2c (4.48 mMol) in ethanol (30 mL) and the mixture was stirred at room temperature overnight. The reaction mixture was filtered and washed with ethanol (20 mL). The filtrate was concentrated and purified on a silica gel column with 15% EtOAc/Hexane to give (9E)-1-(2,4-dichloro-phenyl)-9-(4-fluoro-benzylidene)-4,5,6,7,8,9-hexahydro-1H-cyclooctapyrazole-3-carboxylic acid ethyl ester Compound 2e (0.37 g, 17.5% for last 2 steps).

A solution of LiOH (43 mg, 1.8 mMol) in water (2 mL) was added to a solution of Compound 2e (0.17 g, 0.36 mMol) in a mixture of THF (6 mL) and ethanol (1 mL). The mixture was stirred at room temperature overnight, then concentrated and acidified with 1N HCl (10 mL). The aqueous solution was extracted with EtOAc (100 mL). The organic layer was washed with brine and dried over Na₂SO₄, then filtered and concentrated to give (9E)-1-(2,4-dichloro-phenyl)-9-(4-fluoro-benzylidene)-4,5,6,7,8,9-hexahydro-1H-cyclooctapyrazole-3-carboxylic acid Compound 2f (0.15 g, 93.6%) as a yellow solid.

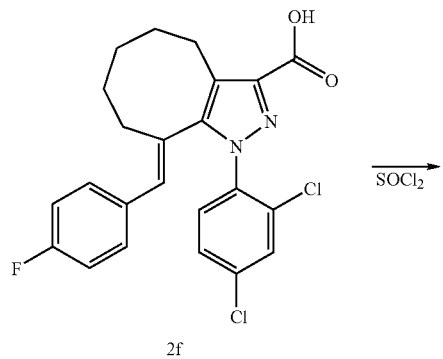

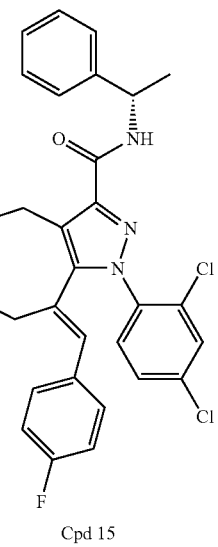

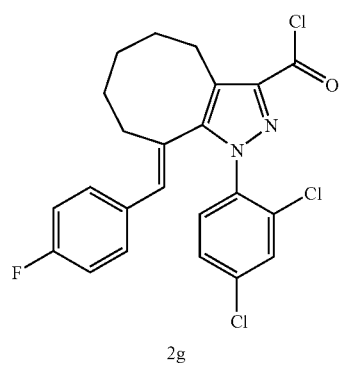

SOCl₂ (0.3 mL, 4.1 mMol) was added to a solution of Compound 2f (0.15 g, 0.34 mMol) in DCM (2 mL). The mixture was refluxed for 3 hrs, then concentrated under high vacuum to give (9E)-1-(2,4-dichloro-phenyl)-9-(4-fluoro-benzylidene)-4,5,6,7,8,9-hexahydro-1H-cyclooctapyrazole-3-carbonyl chloride Compound 2g (0.15 g, 95.3%) as a yellow solid.

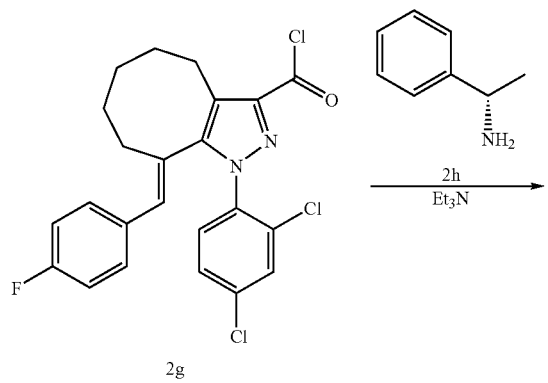

A solution of (1S)-1-phenyl-ethylamine (0.013 g, 0.11 mMol) and TEA (0.03 ml, 0.22 mmol) was added to a solution of Compound 2g (30 mg, 0.065 mMol) in DCM (2 ml). The reaction mixture was stirred at room temperature for 1 hr, diluted with DCM and washed with 1N HCl. The organic layer was washed with water and dried over Na₂SO₄, then filtered and concentrated. The resulting yellow residue was purified on a preparative silica gel plate with 20% EtOAc/Hexane to give Compound 15 (30 mg, 84.2%) as a pale yellow powder. MS m/z 548 (M⁺).

Following the procedure of Example 2, substituting the appropriate starting materials, reagents and solvents, the following compounds were prepared:

| Cpd | Name | MS |
|---|---|---|
| 11 | (9E)-1-(2,4-dichloro-phenyl)-9-(4-fluoro-benzylidene)-4,5,6,7,8,9-hexahydro-1H-cyclooctapyrazole-3-carboxylic acid N'-(2,4-dichloro-phenyl)-hydrazide | 603 |
| 12 | (9E)-1-(2,4-dichloro-phenyl)-9-(4-fluoro-benzylidene)-4,5,6,7,8,9-hexahydro-1H-cyclooctapyrazole-3-carboxylic acid [(1R)-1-phenyl-ethyl]-amide | 548 |
| 13 | (9E)-1-(2,4-dichloro-phenyl)-9-(4-fluoro-benzylidene)-4,5,6,7,8,9-hexahydro-1H-cyclooctapyrazole-3-carboxylic acid [(1R)-1-pyridin-2-yl-ethyl]-amide | 549 |
| 14 | (9E)-[1-(2,4-dichloro-phenyl)-9-(4-fluoro-benzylidene)-4,5,6,7,8,9-hexahydro-1H-cyclooctapyrazol-3-yl]-piperidin-1-yl-methanone | 512 |
| 16 | (9E)-1-(2,4-dichloro-phenyl)-9-(4-fluoro-benzylidene)-4,5,6,7,8,9-hexahydro-1H-cyclooctapyrazole-3-carboxylic acid [(1S)-1-cyclohexyl-ethyl]-amide | 554 |
| 17 | (9E)-1-(2,4-dichloro-phenyl)-9-(4-fluoro-benzylidene)-4,5,6,7,8,9-hexahydro-1H-cyclooctapyrazole-3-carboxylic acid [(1R)-1-cyclohexyl-ethyl]-amide | 554 |
| 18 | (9E)-1-(2,4-dichloro-phenyl)-9-(4-fluoro-benzylidene)-4,5,6,7,8,9-hexahydro-1H-cyclooctapyrazole-3-carboxylic acid (hexahydro-cyclopenta[c]pyrrol-2-yl)-amide | 553 |
| 19 | (9E)-1-(2,4-dichloro-phenyl)-9-(4-fluoro-benzylidene)-4,5,6,7,8,9-hexahydro-1H-cyclooctapyrazole-3-carboxylic acid piperidin-1-ylamide | 527 |

Additional compounds may be made according to the synthetic methods of the present invention by one skilled in the art, differing only in possible starting materials, reagents and conditions used in the instant methods.

Biological Examples

The following examples illustrate that the compounds of the present invention are CB receptor modulators useful for treating, ameliorating or preventing a cannabinoid receptor mediated syndrome, disorder or disease in a subject in need thereof.

Example 1

Binding Assay for CB1 or CB2 Agonists or Inverse Agonists

The human CB1 and CB2 receptors were stably expressed in SK-N-MC cells transfected with pcDNA3 CB-1 (human) or pcDNA3 CB-2 (human). The cells were grown in T-180 cell culture flasks under standard cell culture conditions at 37° C. in a 5% $CO_2$ atmosphere. The cells were harvested by trysinization and homogenized in a homogenization buffer (10 mM Tris, 0.2 mM $MgCl_2$, 5 mM KCl, with protease inhibitors aprotinin, leupeptin, pepstatin A and bacitracin) and centrifuged (2000 g). The supernatant was then centrifuged in 2M sucrose (31,300 g) to produce a semi-purified membrane pellet. The pellet was resuspended in homogenization and stored at −80° C.

On the day of the assay, the pellet was thawed on ice and diluted in assay buffer (50 mM Tris-HCl, 5 mM $MgCl_2$, 2.5 mM EDTA, 0.5 mg/mL fatty acid free bovine serum albumin, pH 7.5). The diluted membrane pellet was added with buffer, either a test compound or vehicle standard and the radioligand $[H]^{3+}$-CP-55,940 (0.2 nM) to the wells of a 96-well polypropylene plate. Non-specific binding was measured in wells containing WIN 55,212 (10 uM). The plate was covered and incubated for 90 minutes at 30° C. The contents were then aspirated onto a Packard Unifilter GF/C filter bottom plate prewet with 0.5% polyethyleneimine The wells of the polypropylene plate were rinsed and aspirated seven times with a 0.9% saline-0.5% Tween 20 solution. The Unifilter plate was dried, scintillation cocktail was added to each well and the counts representing binding were quantitated in a TopCount scintillation counter.

CB1 and CB2 Receptor Binding Results

For compounds tested, an $IC_{50}$ binding value was obtained from percent inhibition studies in which various test concentrations were used. The binding value was calculated by linear regression.

For compounds without an $IC_{50}$ binding value, the percent inhibition (%) was obtained at a test concentration of [1] 10 μM, [2] 1 μM, [3] 0.2 μM, [4] 0.003 μM, [5] represents an average value.

TABLE 1

Cannabinoid CB1 Receptor Binding $IC_{50}$ (μM)

| Cpd | $IC_{50}$ |
| --- | --- |
| 1 | 0.04 |
| 2 | 0.04, 0.5, 0.3, 0.2 2.1 |
| 3 | [1] 45% |
| 4 | 0.06 |
| 5 | [1] 47% |
| 6 | 0.3, [2] 86% |
| 11 | [3] 56% |
| 12 | 0.008, [3] 89% |
| 13 | 0.008, [3] 90% |
| 14 | [3] 50% |
| 15 | [5] 50% |
| 16 | [5] 59% |
| 17 | 0.01, [3] 86% |
| 18 | 0.05, [5] 73% |
| 19 | [5] 65% |

TABLE 2

Cannabinoid CB2 Receptor Binding $IC_{50}$ (μM)

| Cpd | $IC_{50}$ |
| --- | --- |
| 1 | 0.0001, 0.00009 |
| 2 | 0.001, 0.006, 0.01, [4] 86% |
| 3 | 0.02 |
| 4 | [4] 74% |
| 5 | 0.1 |
| 6 | 0.0006, 0.0007, [2] 91% |
| 11 | [3] 30% |
| 12 | [3] 18% |
| 13 | [3] 11% |
| 14 | [3] 28% |
| 15 | [5] 25% |
| 16 | [5] 20% |
| 17 | [3] 25% |
| 18 | [5] 44% |
| 19 | [5] 33% |

Example 2

Functional Cell-Based Assay for CB1 or CB2 Agonist and Inverse Agonist Effects on Intra-Cellular Adenylate Cyclase Activity The CB1 and CB2 receptors are G-protein coupled receptors (GPCR), which influence cell function via the Gi-protein. These receptors modulate the activity of intracellular adenylate cyclase, which in turn produces the intracellular signal messenger cyclic-AMP (cAMP).

At baseline, or during non-ligand bound conditions, these receptors are constitutively active and tonically suppress adenylate cyclase activity. The binding of an agonist causes further receptor activation and produces additional suppression of adenylate cyclase activity. The binding of an inverse agonist inhibits the constitutive activity of the receptors and results in an increase in adenylate cyclase activity.

By monitoring intracellular adenylate cyclase activity, the ability of compounds to act as agonists or inverse agonists can be determined Assay Test compounds were evaluated in SK-N-MC cells which, using standard transfection procedures, were stably transfected with human cDNA for pcDNA3-CRE β-gal and pcDNA3 CB1 receptor (human) or pcDNA3 CB2 receptor (human). By expressing CRE β-gal, the cells produced β-galactosidase in response to CRE promoter activation by cAMP. Cells expressing CRE β-gal and either the human CB1 or CB2 receptor will produce less β-galactosidase when treated with a CB1/CB2 agonist and will produce more β-galactosidase when treated with a CB1/CB2 inverse agonist.

Cell Growth

The cells were grown in 96-well plates under standard cell culture conditions at 37° C. in a 5% $CO_2$ atmosphere. After 3 days, the media was removed and a test compound in media (wherein the media was supplemented with 2 mM L-glutamine, 1M sodium pyruvate, 0.1% low fatty acid FBS (fetal bovine serum) and antibiotics) was added to the cell. The plates were incubated for 30 minutes at 37° C. and the plate cells were then treated with forskolin over a 4-6 hour period, then washed and lysed. The β-galactosidase activity was quantitated using commercially available kit reagents (Promega Corp. Madison, Wis.) and a Vmax Plate Reader (Molecular Devices, Inc).

CB1 Receptor Mediated Change in CRE β-gal Expression

For cells expressing CRE β-gal and the CB1 receptor, CB1 agonists reduced β-galactosidase activity in a dose-dependent manner and CB1 inverse agonists increased β-galactosidase activity in a dose-dependent manner.

The change in β-galactosidase activity was determined by setting a vehicle treated cell's activity value at 100% and expressing the β-galactosidase activity measured in a corresponding compound treated cell as a percent of the vehicle treated cell activity.

CB1 Receptor Results

The $EC_{50}$ value for functional activity for compounds tested was calculated by linear regression and was obtained from studies in which varying compound concentrations were used. Data provided for certain compounds is represented by percent change (%) in functional activity at a single test concentration: [1] 10 μM and [2] 1 μM.

TABLE 3

| CB1 Receptor Functional Activity $EC_{50}$ (μM) | |
|---|---|
| Cpd | $EC_{50}$ |
| 1 | [1] −78% |
| 2 | [2] −71% |
| 3 | [1] −6% |
| 4 | [2] −71% |
| 5 | [1] 10% |
| 12 | 0.01 |
| 13 | 0.002 |
| 17 | 0.04 |
| 18 | 0.02 |

CB2 Receptor Mediated Change in CRE β-gal Expression

For cells expressing CRE β-gal and the CB2 receptor, CB2 agonists reduced β-galactosidase activity in a dose-dependent manner and CB2 inverse agonists increase β-galactosidase activity in a dose-dependent manner.

The change in β-galactosidase activity was determined by setting a vehicle treated cell's activity value at 100% and expressing the β-galactosidase activity measured in a corresponding compound treated cell as a percent of the vehicle treated cell activity.

CB2 Receptor Results

The $EC_{50}$ value for functional activity for compounds tested was calculated by linear regression and was obtained from studies in which varying compound concentrations were used.

The value of 29% for Compound 5 represents change in functional activity and was obtained from a study in which one compound concentration was used.

TABLE 4

| CB2 Receptor Functional Activity $EC_{50}$ (μM) | |
|---|---|
| Cpd | $EC_{50}$ |
| 1 | 0.0016 |
| 2 | 0.0066 |
| 3 | 0.2 |
| 6 | 0.029 |

Example 4

Oil of Mustard Induced Colitis Model

In the distal colon, the oil of mustard colitis model is characterized by a discontinuous pattern of mucosal epithelial damage, submucosal edema, infiltration of inflammatory cells (including macrophages, neutrophils and lymphocytes) into the mucosa and submucosa, increased wet weight of the colon, shrinkage of the colon length, diarrhea and apparent inflammation (see, Kimball E. S., Palmer J. M., D'Andrea M. R., Hornby P. J. and Wade P. R., Acute colitis induction by oil of mustard results in later development of an IBS-like accelerated upper GI transit in mice, *Am. J. Physiol. Gastrointest. Liver Physiol.*, 2005, 288: G1266-1273).

Colitis Induction

Male CD-1 mice (Charles River Laboratories, Kingston, N.C.)(9-11 weeks old) and fresh oil of mustard (OM) (allyl isothiocyanate, 98% purity, Sigma-Aldrich St. Louis, Mo.) were used.

The mice (9 per treatment group) were briefly anesthetized with ketamine/xylasine (Sigma, St. Louis, Mo.) and a solution of 0.5% OM in 30% ethanol (50 μL) was administered intracolonically (to a depth of 4 cm) via syringe (equipped with a ball-tipped 22 G needle).

A test compound was orally administered one day prior to colitis induction for assessing a prophylactic regimen or one day post-induction for assessing a therapeutic regimen. A test compound was orally administered daily thereafter. Two days after OM administration, the last test compound dose was administered.

Three days after OM administration, the animals were sacrificed. The colons were resected, examined for signs of inflammation, weighed after removing fecal contents and the length from the aboral end of the cecum to the anus was measured. The fecal contents were examined for signs of diarrhea. The distal colon between the $1^{st}$ and the $4^{th}$ centimeter was removed and placed in 10% neutral buffered formalin for histological analysis.

Macroscopic Observations and Criteria

The macroscopic observations of colon inflammation (a measure of colon damage), colon weight and length and stool consistency and appearance were assigned a score and used to evaluate colitis severity.

The four observation scores for each colon were combined, whereby a combined score of 0 represents a normal colon and a combined score of 15 represents a maximally affected colon. Statistical analyses were performed in Graphpad Prism 4.0 using ANOVA.

|  | 0 | 1 | 2 | 3 | 4 |
|---|---|---|---|---|---|
|  | | | Weight Score | | |
| Weight Gain | <5% | 5-14% | 15-24% | 25-35% | >35% |
|  | | | Length Score | | |
| Shortening | <5% | 5-14% | 15-24% | 25-35% | >35% |
|  | | | Stool Score | | |
|  | 0 | 1 | 2 | 3 | |
| Fecal Pellet Formation | normal (well-formed) | loosely-shaped, moist | amorphous, moist, sticky | diarrhea | |
|  | | | Damage Score | | |
|  | 0 | 1 | 2 | 3 | 4 |
| Inflammation | none observed | mild, localized erythema | moderate, more widely distributed erythema | severe, extensively distributed erythema | penetrating ulcers, bloody lesions |

Microscopic (Histological) Examination

Histological analyses of tissues consisted of staining paraffin-embedded tissue sections with hematoxylin-eosin dye. The tissues were examined using light microscopy by an investigator who was blinded to the sample groups.

Histological Observations and Criteria

The microscopic observations of epithelial damage, cellular infiltration and damage or alteration of smooth muscle architecture (a measure of muscle damage) were assigned a score and used to evaluate colitis severity.

The scores for each colon were combined, whereby a combined score of 0 represents a normal colon and a combined score of 9 represents a maximally affected colon. Statistical analyses were performed in Graphpad Prism 4.0 using ANOVA.

Criteria and Observations

|  | 0 | 1 | 2 | 3 |
|---|---|---|---|---|
|  | | Epithelial Damage Score | | |
| Epithelium Loss | intact | ≦⅓ loss | >⅓ to ⅔ loss | >⅔ loss |
|  | | Cellular Infiltration Score | | |
| Focal Areas of Infiltration | none | 1-2 focal areas | >2 focal areas | N/A |
| Infiltrated Cell Presence | none | ≦⅓ of entire colon length | >⅓ to ⅔ of entire colon length | ≧⅔ of entire colon length |
|  | | Architecture Score | | |
| Muscle Damage (any evidence of edema, hyperplasia or loss of architecture) | no damage observed | ≦⅓ of entire colon length | ≦⅔ of entire colon length | ≧⅔ of entire colon length |

Prophylactic and Therapeutic Colitis Treatment Regimen Results

The Macroscopic Score and Microscopic Score results for each treatment group in the prophylactic and therapeutic regimens were each combined into a mean score and expressed as % inhibition of colitis (% Inh). Test (#) represents the number of experiments at each dose level.

TABLE 1

Prophylactic Regimen

| Cpd | Dose (mg/kg) | Test (#) | % Inh (Macro) | % Inh (Micro) |
|---|---|---|---|---|
| 2 | 5 | 1 | 42.3 ± 12.6 | 74.4 ± 3.8 |

TABLE 2

Therapeutic Regimen

| Cpd | Dose (mg/kg) | Test (#) | % Inh (Macro) | Test (#) | % Inh (Micro) |
|---|---|---|---|---|---|
| 2 | 5 | 3 | 38.7 ± 9.1 | 1 | 66.0 ± 9.8 |

Example 5

Dextran Sulfate Sodium (DSS) Induced Colitis Model

In the distal colon, the DSS colitis model is characterized by a discontinuous pattern of mucosal epithelial damage, infiltration of inflammatory cells (including macrophages, neutrophils and lymphocytes) into the mucosa and submucosa, decreased wet weight of the colon, shrinkage of the colon length and diarrhea (see, Blumberg R. S., Saubermann L. J. and Strober W., Animal models of mucosal inflammation and their relation to human inflammatory bowel disease, *Current Opinion in Immunology,* 1999, Vol. 11: 648-656; Egger B., Bajaj-Elliott M., MacDonald T. T., Inglin R., Eysselein, V. E. and Buchler M. W., Characterization of acute murine dextran sodium sulphate colitis: Cytokine profile and dose dependency, *Digestion,* 2000, Vol. 62: 240-248; Stevceva L., Pavli P., Husband A. J. and Doe, W. F., The inflammatory infiltrate in the acute stage of the dextran sulphate sodium induced colitis: B cell response differs depending on the percentage of DSS used to induce it, *BMC Clinical Pathology,* 2001, Vol 1: 3-13; and Diaz-Granados, Howe K., Lu J. and McKay D. M., Dextran sulfate sodium-induced colonic histopathology, but not altered epithelial ion transport, is reduced by inhibition of phosphodiesterase activity, *Amer. J. Pathology,* 2000, Vol. 156: 2169-2177).

Colitis Induction

Female Balb/c mice (Taconic Farms, Germantown, N.Y.) (10-13 weeks old) were provided with a solution of 5% DSS (45 kD molecular weight, ICN chemicals, Newport, Calif.) in tap water ad libitum over a 7-day period. The DSS solution was replenished daily and the amount consumed was measured.

The mice (10 per treatment group) were orally administered a test compound on the day of colitis induction and then daily thereafter.

Six days after the initial DSS administration, the last test compound dose was administered.

Seven days after the initial DSS administration, the animals were sacrificed. The colons were resected, examined for signs of inflammation, weighed after removing fecal contents and the length from the aboral end of the cecum to the anus was measured. The fecal contents were examined for signs of diarrhea. The distal colon between the $1^{st}$ and the $4^{th}$ centimeter was removed and placed in 10% neutral buffered formalin for histological analysis.

Macroscopic Observations and Criteria

The macroscopic observations of colon inflammation (a measure of colon damage), colon length and stool consistency and appearance were assigned a score and used to evaluate colitis severity.

The three observation scores for each colon were combined, whereby a combined score of 0 represents a normal colon and a combined score of 11 represents a maximally affected colon. Statistical analyses were performed in Graphpad Prism 4.0 using ANOVA.

|  | 0 | 1 | 2 | 3 | 4 |
|---|---|---|---|---|---|
|  | Weight Score | | | | |
| Weight Gain | <5% | 5-14% | 15-24% | 25-35% | >35% |
|  | Length Score | | | | |
| Shortening | <5% | 5-14% | 15-24% | 25-35% | >35% |
|  | Stool Score | | | | |
|  | 0 | 1 | 2 | 3 | |
| Fecal Pellet Formation | normal (well-formed) | loosely-shaped, moist | amorphous, moist, sticky | severe diarrhea | |
|  | Damage Score | | | | |
|  | 0 | 1 | 2 | 3 | 4 |
| Inflammation | none observed | mild, reddening observed | moderate, more widely distributed reddening | severe, extensively distributed reddening | penetrating ulcers, bloody lesions |

Microscopic (Histological) Examination

Histological analyses of tissues consisted of staining paraffin-embedded tissue sections with hematoxylin-eosin dye. The tissues were examined using light microscopy by an investigator who was blinded to the sample groups.

Histological Observations and Criteria

The microscopic observations of epithelial damage, cellular infiltration and damage or alteration of smooth muscle architecture (a measure of muscle damage) were assigned a score and used to evaluate colitis severity.

The scores for each colon were combined, whereby a combined score of 0 represents a normal colon and a combined score of 9 represents a maximally affected colon. Statistical analyses were performed in Graphpad Prism 4.0 using ANOVA.

Criteria and Observations

|  | 0 | 1 | 2 | 3 |
|---|---|---|---|---|
|  | Epithelial Damage Score | | | |
| Epithelium Loss | intact | ≦⅓ loss | >⅓ to ⅔ loss | >⅔ loss |
|  | Cellular Infiltration Score | | | |
| Focal Areas of Infiltration | none | 1-2 focal areas | >2 focal areas | N/A |
| Infiltrated Cell Presence | none | ≦⅓ of entire colon length | >⅓ to ⅔ of entire colon length | ≧⅔ of entire colon length |
|  | Architecture Score | | | |
| Muscle Damage (any evidence of edema, hyperplasia or loss of architecture) | no damage observed | ≦⅓ of entire colon length | ≦⅔ of entire colon length | ≧⅔ of entire colon length |

Colitis Treatment Regimen Results

The Macroscopic Score and Microscopic Score results for each treatment group were each combined into a mean score and expressed as % inhibition of colitis (% Inh). Test (#) represents the number of experiments at each dose level. ND represents Not Determined.

TABLE 1

| Cpd | Dose (mg/kg) | Test (#) | % Inh (Macro) | % Inh (Micro) |
|---|---|---|---|---|
| 2 | 1 | 1 | −4.3 ± 12.9 | ND |
| 2 | 5 | 1 | 21.9 ± 15.2 | 75.7 ± 8.9 |
| 2 | 10 | 1 | 50.5 ± 9.0 | ND |
| 2 | 20 | 1 | 31.6 ± 8.5 | ND |

It is to be understood that the preceding description of the invention and various examples thereof have emphasized certain aspects. Numerous other equivalents not specifically elaborated on or discussed may nevertheless fall within the spirit and scope of the present invention or the following claims and are intended to be included.

What is claimed is:

1. A method for treating a cannabinoid receptor mediated syndrome, disorder or disease in a subject in need thereof comprising the step of administering to the subject an effective amount of a compound of formula (1):

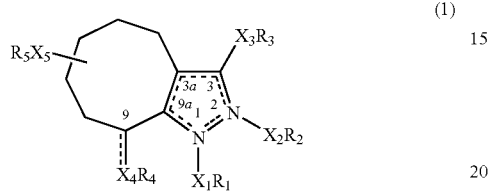

or a salt, isomer, prodrug, metabolite or polymorph thereof
wherein the dashed lines between positions 2-3 and positions 3a-9a in formula (I) represent locations for each of two double bonds present when $X_1R_1$ is present;
the dashed lines between positions 3-3a and positions 9a-1 in formula (I) represent locations for each of two double bonds present when $X_2R_2$ is present;
the dashed line between position 9 and $X_4R_4$ in formula (I) represents the location for a double bond;
$X_1$ is absent or lower alkylene;
$X_2$ is absent or lower alkylene;
wherein only one of $X_1R_1$ and $X_2R_2$ are present;
$X_3$ is absent, lower alkylene, lower alkylidene or —NH—;
when the dashed line between position 9 and $X_4R_4$ is absent, $X_4$ is absent or lower alkylene;
when the dashed line between position 9 and $X_4R_4$ is present, $X_4$ is absent;
$X_5$ is absent or lower alkylene;
$R_1$ is selected from hydrogen, alkyl (optionally substituted at one or more positions by halogen, hydroxy or lower alkoxy), lower alkyl-sulfonyl, aryl, $C_3$-$C_{12}$ cycloalkyl or heterocyclyl, wherein aryl, $C_3$-$C_{12}$ cycloalkyl or heterocyclyl is each optionally substituted at one or more positions by halogen, aminosulfonyl, lower alkyl-aminosulfonyl, alkyl (optionally substituted at one or more positions by halogen, hydroxy or lower alkoxy), hydroxy or alkoxy (optionally substituted at one or more positions by halogen or hydroxy);
$R_2$ is selected from hydrogen, alkyl (optionally substituted at one or more positions by halogen, hydroxy or lower alkoxy), lower alkyl-sulfonyl, aryl, $C_3$-$C_{12}$ cycloalkyl or heterocyclyl, wherein aryl, $C_3$-$C_{12}$ cycloalkyl or heterocyclyl is each optionally substituted at one or more positions by halogen, aminosulfonyl, lower alkyl-aminosulfonyl, alkyl (optionally substituted at one or more positions by halogen, hydroxy or lower alkoxy), hydroxy or alkoxy (optionally substituted at one or more positions by halogen or hydroxy);
$R_3$ is —C(O)—$Z_1$($R_6$), —$SO_2$—$NR_7$—$Z_2$($R_8$) or —C(O)—$NR_9$—$Z_3$($R_{10}$);
when the dashed line between position 9 and $X_4R_4$ is absent, $X_4$ is absent or lower alkylene and $R_4$ is hydrogen, hydroxy, lower alkyl, lower alkoxy, halogen, aryl, $C_3$-$C_{12}$ cycloalkyl or heterocyclyl, wherein aryl, $C_3$-$C_{12}$ cycloalkyl or heterocyclyl is each optionally substituted at one or more positions by hydroxy, oxo, lower alkyl (optionally substituted at one or more positions by halogen, hydroxy or lower alkoxy), lower alkoxy (optionally substituted at one or more positions by halogen or hydroxy) or halogen;
when the dashed line between position 9 and $X_4R_4$ is present, $X_4$ is absent and $R_4$ is CH-aryl or CH-heterocyclyl, wherein aryl or heterocyclyl is each optionally substituted at one or more positions by hydroxy, oxo, lower alkyl, lower alkoxy or halogen;
$R_5$ is absent, hydroxy, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl;
$R_6$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl;
$R_7$ is hydrogen or lower alkyl;
$R_8$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aryl, aryloxy, arylalkoxy or heterocyclyl;
$R_9$ is hydrogen or lower alkyl;
$R_{10}$ is aryl, $C_3$-$C_{12}$ cycloalkyl or heterocyclyl, wherein aryl, $C_3$-$C_{12}$ cycloalkyl or heterocyclyl is each optionally substituted by one or more hydroxy, oxo, halogen, amino, aminoalkyl, alkyl (optionally substituted at one or more positions by halogen, hydroxy or lower alkoxy), alkoxy (optionally substituted at one or more positions by halogen or hydroxy), carboxy, carbonylalkoxy, carbamoyl, carbamoylalkyl, aminosulfonyl, lower alkyl-aminosulfonyl, aryl, aryloxy, arylalkoxy or heterocyclyl;
$Z_1$ and $Z_2$ is each absent or alkyl; and,
$Z_3$ is absent, —NH—, —$SO_2$— or alkyl (wherein alkyl is optionally substituted at one or more positions by halogen, hydroxy, lower alkyl, lower alkoxy, carboxy or carbonylalkoxy).

2. The method of claim 1 wherein the cannabinoid receptor is a CB1 or CB2 receptor; and, the compound of Formula 1 is an agonist, antagonist or inverse-agonist of the receptor.

3. The method of claim 1 wherein the syndrome, disorder or disease is related to appetite, metabolism, diabetes, glaucoma-associated intraocular pressure, social and mood disorders, seizures, substance abuse, learning, cognition or memory, organ contraction or muscle spasm, bowel disorders, respiratory disorders, locomotor activity or movement disorders, immune and inflammation disorders, unregulated cell growth, pain management or neuroprotection.

4. The method of claim 1 wherein the effective amount of the compound of Formula 1 is from about 0.001 mg/kg/day to about 300 mg/kg/day.

5. The method of claim 1 further comprising treating a CB1 receptor inverse-agonist mediated appetite related, obesity related or metabolism related syndrome, disorder or disease in a subject in need thereof comprising the step of administering to the subject an effective amount of a CB1 inverse-agonist compound of Formula 1.

6. The method of claim 5 wherein the effective amount of the compound of Formula 1 is from about 0.001 mg/kg/day to about 300 mg/kg/day.

7. The method of claim 1 further comprising the step of administering to the subject a combination product and/or therapy comprising an effective amount of a compound of Formula 1 and a therapeutic agent.

8. The method of claim 7 wherein the therapeutic agent is an anticonvulsant or a contraceptive agent.

9. The method of claim 8 wherein the anticonvulsant is topiramate, analogs of topiramate, carbamazepine, valproic acid, lamotrigine, gabapentin, phenyloin and the like and mixtures or pharmaceutically acceptable salts thereof.

10. The method of claim 8 wherein the contraceptive agent is a progestin-only contraceptive, a contraceptive having a progestin component and an estrogen component, or an oral contraceptive optionally having a folic acid component.

* * * * *